United States Patent
Cao

(10) Patent No.: US 6,331,111 B1
(45) Date of Patent: Dec. 18, 2001

(54) CURING LIGHT SYSTEM USEFUL FOR CURING LIGHT ACTIVATED COMPOSITE MATERIALS

(75) Inventor: Densen Cao, Sandy, UT (US)

(73) Assignee: Cao Group, Inc., Sandy, UT (US)

( * ) Notice: Subject to any disclaimer, the term of this patent is extended or adjusted under 35 U.S.C. 154(b) by 0 days.

(21) Appl. No.: 09/405,373

(22) Filed: Sep. 24, 1999

(51) Int. Cl.⁷ .................................................. A61C 1/00
(52) U.S. Cl. ........................ 433/29; 362/800; 362/804; 362/119; 606/16
(58) Field of Search ........................ 433/29, 215; 606/1, 606/13, 16; 607/88; 362/800, 804, 119

(56) References Cited

U.S. PATENT DOCUMENTS

| | | | |
|---|---|---|---|
| D. 361,382 | 8/1995 | Brunsell et al. .................... 24/177 |
| D. 385,051 | 10/1997 | Wu ........................................ D26/2 |
| D. 385,630 | 10/1997 | Lieb et al. ......................... D24/177 |
| 4,221,994 | 9/1980 | Friedman et al. .................... 315/224 |
| 4,666,406 | 5/1987 | Kanca, III .......................... 433/229 |
| 4,935,665 | * 6/1990 | Murata . |
| 4,963,798 | * 10/1990 | McDermott . |
| 4,989,217 | 1/1991 | Ostler ................................. 372/107 |
| 5,115,761 | 5/1992 | Hood .................................. 118/641 |
| 5,161,879 | 11/1992 | McDermott ........................ 362/206 |
| 5,214,658 | 5/1993 | Ostler ................................... 372/23 |
| 5,233,283 | 8/1993 | Kennedy ............................... 320/13 |
| 5,328,368 | * 7/1994 | Lansing et al. ...................... 433/29 |
| 5,415,543 | 5/1995 | Rosmazl, Jr. ......................... 433/29 |
| 5,420,768 | 5/1995 | Kennedy ............................. 362/119 |
| 5,521,392 | 5/1996 | Kennedy et al. .................. 250/492.1 |
| 5,550,853 | 8/1996 | Ostler ................................... 372/34 |
| 5,616,141 | 4/1997 | Cipolla ................................. 606/15 |
| 5,634,711 | 6/1997 | Kennedy et al. .................. 362/119 |
| 5,660,461 | * 8/1997 | Ignatius et al. . |
| 5,698,866 | * 12/1997 | Doiron et al. . |
| 5,803,729 | 9/1998 | Tsimerman ........................... 433/29 |
| 5,890,794 | 4/1999 | Abtahi et al. ....................... 362/294 |
| 5,912,470 | 6/1999 | Eibofner et al. .................. 250/504 H |
| 6,008,264 | 12/1999 | Ostler ..................................... 522/4 |
| 6,019,482 | * 2/2000 | Everett .............................. 362/800 |
| 6,077,073 | 6/2000 | Jacob .................................... 433/29 |
| 6,095,661 | * 8/2000 | Lebens et al. ...................... 362/800 |
| 6,102,696 | * 8/2000 | Osterwalder et al. ................ 433/29 |

FOREIGN PATENT DOCUMENTS

99/35995 * 7/1999 (WO) .

OTHER PUBLICATIONS

ZAP Dual Curing advertisement from Soft–Core Texas, Inc. (no date).

(List continued on next page.)

*Primary Examiner*—Ralph A. Lewis
(74) *Attorney, Agent, or Firm*—Daniel McCarthy

(57) ABSTRACT

A curing light system useful for curing light activated composite materials is disclosed. The system may be a hand-held portable curing light system operated by batteries or a chair side curing light system operated by AC power. The curing light system includes a light source which may be one or more light emitting diode chips or one or more diode laser chips. The chips of the light source are located on a single heat sink for heat dissipation. The heat sink and chips are located in an encasement that may include a focus dome or transparent window through which light travels to reach light activated composite materials. In the preferred embodiment, the light travels from the light source directly to a curing surface without first going through a light guide or fiber optic cable. The light source is preferably located in a handle that is manipulated by a user in order to direct light emitted by the light source to composite materials to be cured. The light source may emit multiple wavelengths of light so that numerous composite materials having photo-initiators sensitive to different wavelengths may all be cured with a single curing light system.

36 Claims, 17 Drawing Sheets

OTHER PUBLICATIONS

Luma–Lite website (http://www.luma–lite.com) pages concerning LumaCare, LumaArch, and Luma 8 (3 pages, Jan. 2001).

Clinical Research Associates Newsletter, vol. 10, Jun. 1986 (Visible–Curing Lights article).

Clinical Research Associates Newsletter, vol. 20, Mar., 1996 (Intraoral Resin Curing Lights article).

LaserMed AGD Show Special AccuCure 3000 Laser Show Special brochure.

LaserMed AccuCure 1000 brochure.

LaserMEd AccurCure 3000 brochure.

"Update on Dental Composite Restorations", Journal of the Americal Dental Association, vol. 125, Jun. 1994, pp. 687–701.

* cited by examiner

CURING LIGHT SYSTEM USEFUL FOR CURING LIGHT ACTIVATED COMPOSITE MATERIALS

I. BACKGROUND OF THE INVENTION

A. Field of the Invention

The invention relates to the field of curing lights that may be used to cure light activated composite materials. The preferred embodiment of the invented curing light system includes a light source that uses semiconductor lasers or light emitting diodes (LED's) to create light and an electronic control module. The system may be a portable hand-held unit that operates by battery power, or a non-portable unit that uses AC power from a standard wall socket.

More particularly, some preferred embodiments of the invention use light sources such as semiconductor lasers and light emitting diodes which can initiate curing of composite materials. Some of the more preferred embodiments of the invention include a light source that has a plurality of individual semiconductor diode laser chips or light emitting diode chips arranged on a single heat sink. In some embodiments of the invention, diode lasers or light emitting diodes may be arranged in an array on an appropriate base or fixture in order to provide greater light power. A housing for the heat sink and laser diode chips or light emitting diode chips may be provided, and the housing may include a light focus dome or a transparent window through which light travels before striking a composite material to be cured. When an array of laser or light emitting diode chips is used, a light with single or multiple wavelength can be achieved by placing the chips with different wavelength in the array. Thus, the light can be used to curing different composites with different photoinitiators.

Some preferred embodiments of the invention relate to a packaged laser or light emitting diode light source seated on a larger heat sink with electrode channels. In some embodiments of the invention, portion of light is a flexible fixture that may be bent in any desired direction for ease of use.

When the invention is used, light emitted from it can be directly applied to a curing surface without first traveling through a light guide, light focus means or fiber optics as used in prior art. Alternatively, a light guide, light focus means, fiber optics or other optics may be used with the system.

One preferred embodiment of the invention uses rechargeable DC batteries as a power source. That configuration facilitates portability. A battery charger is provided in that embodiment to charge the batteries and to power the system if it is desired to operate the system from a non-mobile power source. Another preferred embodiment of the invention is receives power from a cord attached to an AC power source outlet. Some of the more preferred embodiments of the invention include an electronic control module to control light output time and light intensity, and to monitor battery status.

B. The Background Art

In the prior art, various light sources have been used for the purpose of curing composite materials. Traditionally, the light source for a curing light is a filtered high power halogen, fluorescent, and arch lamps. A light guide is typically used to deliver the light to the surface of composite materials to be cured. That and other prior art is described below.

In U.S. Pat. No. 4,221,994 a curing light is disclosed which uses a fluorescent lamp to harden photosensitive reactants such as dental restorative material. U.S. Pat. No. 4,666,406 discloses a light guide for use in composite curing. U.S. Pat. No. 5,115,761 describes a chamber for curing adhesives. U.S. Pat. No. 5,415,543 discloses a curing light apparatus using an actinic light source with inert gas and a light guide. U.S. Pat. Nos. Des. 361,382 and Des. 385,630 disclose aesthetic designs for curing light systems. U.S. Pat. No. 5,616,141 discloses a laser system for use in dental procedures. U.S. Pat. No. 5,803,729 discloses a curing light system with a light guide that uses a light bulb with filtering.

The prior art described above suffers from several disadvantages: 1.) High power halogen lamps generate a large amount of heat. The heat might be transferred to a composite surface being cured, causing the material to deform. The heat can also cause discomfort to a patient if the curing light is being used in medicine or dentistry. 2.) Systems which generate large amounts of heat require a cooling system. Typically a cooling fan, gas coolant, or liquid coolant is used to dissipate generated in prior art curing light systems. A cooling fan creates substantial noise and is therefore undesirable. Gas and liquid coolant increase system size, weight, complexity and cost. 3.) Commercially viable prior art systems are large in size. 4.) Systems which use ordinary AC power rather than DC battery power tend to have greater circuit complexity and are not portable. (see Clinical Research Associates Newsletter Volume 10, June 1986, Volume 20, March 1996), A portable curing light system using battery power and a filtered halogen light source has been marketed by L.D Caulk/Dentsply of Milford, Del. That system is relatively large in size and has some of the disadvantages listed above.

Solid-state lasers have been used as a light source for curing lights. For example, U.S. Pat. No. 5,616,141 discloses a curing light apparatus using argon ions as its light source. There are advantages to curing by use of laser light compared to curing by use of different lamps. Laser curing tends to be faster, generates less heat and provides superior characteristics in the cured composite. However, argon laser systems are disadvantageous compared to semiconductor laser systems because argon laser systems are large, need appropriate cooling devices, and are expensive to manufacture.(See Clinical Research Newsletter Volume 20, March 1996)

A curing light system that uses light emitting diodes as a light source is disclosed in U.S. Pat. No. 5,420,768. That system includes a packaged LED array and a light guide. The disclosure is vague and incomplete, however, in that no detailed description is provided concerning light source construction or the control system. Light emitting diodes have been used as light sources in other applications in the prior art. See, for example, U.S. Pat. Nos. Des. 395,051; 5,890,794; and 5,161,879.

Therefore the prior art has shown a need for a curing light for light activated composite materials which provides some or all of the following features in combination: portability, light weight, inexpensive, little heat generation, no need for cooling system, no need for complicated circuitry, and novel semiconductor laser and LED light sources.

Each of the foregoing references is hereby incorporated by reference for the material disclosed therein.

II. OBJECTS OF THE INVENTION

It is an object of some embodiments of the invention to provide a curing light system that uses semiconductor lasers and/or light emitting diodes as a light source. Preferred embodiments of the invention include novel LED and novel laser diode chip light sources. The light generated by the light sources may be used to cure composite materials such as those used in dentistry and medicine.

It is an object of some embodiments of the invention to provide a curing light with plurality of diode laser or LED chips on a single heat sink. Providing a plurality of chips on a single heat sink decreases both size and manufacturing cost of the curing light system.

It is an object of some embodiments of the invention to provide a curing light system using surface emitting diode laser chips or edge emitting diode laser chips. As described below, surface emitting and edge emitting diode laser chips may be used as a light source in the invention.

It is an object of some embodiments of the invention to provide a two dimensional array of diode lasers or light emitting diodes. The array may be pre-built in a housing in a compact or closely-packed manner. The number of lasers or LED's may be adjusted depending on space and power requirements. Use of an array allows light of greater intensity to be efficiently delivered from a compact light source to a curing surface. Use of an array also allows the light beam with different wavelength to cure different composite materials with different photoinitiators.

It is an object of some embodiments of the invention to provide a functional housing for a heat sink and its corresponding laser diode chips or light emitting diode chips. Some preferred housings include sealed plastic and sealed metal housings with a window. The housing may include a focus dome for focusing light emitted by the laser diodes or the light emitting diodes. The focus dome can focus light before delivering it to a remote location. Alternatively, the housing may include a transparent window to permit light to escape from the housing for delivery to a remote location. The housing will therefore serve to protect the light source, and may also serve to focus light before it is delivered to a remote location. Electrodes providing power to laser or LED chips are present in the housing.

It is an object of some embodiments of the invention to provide a curing light system in which a light source, control circuitry, user interface, and batteries are all contained with a single hand-held unit. Such a portable curing light system is made possible by the invention.

It is an object of some embodiments of the invention to provide a non-portable chairside curing light system that includes a handpiece of small size, with power and control circuitry remotely located. An embodiment of the invention is utilizing AC power as power source and has a handpiece containing the light source and an on/off button or trigger, but has power and control circuitry in a separate module to which the handpiece is connected by cabling.

It is an object of some embodiments of the invention to provide efficient heat dissipation. In some embodiments of the invention, single or multiple LED chips or laser diode chips are located on a single heat sink. The heat sink dissipates heat generated by the LED or laser diode chips so that a separate cooling system such as a fan or liquid coolant is not required.

It is an object of some embodiments of the invention to provide an LED or laser diode chip in a well on a heat sink. Light emitted from the side(s) of the LED or laser diode chip may be reflected off the walls of the well so that it will travel in a desired direction.

It is an object of some embodiments of the invention to provide a curing light system capable of emitting light of more than one wavelength in order to cure more than one type of composite material. An array of LED's or laser diode chips may be assembled including chips capable of emitting different desired wavelengths of light may be incorporated into the light source to achieve this.

It is an object of some embodiments of the invention to provide a light source that has LED's or laser diode chips both on a face of a heat sink and around the periphery of that face of the heat sink. Consequently, more LED's or laser diode chips may be placed on the heat sink either to achieve a more powerful light or to accommodate the necessary number of wavelengths of light that are desired to be produced.

It is an object of the invention to provide embodiments of curing light systems that operate by DC battery power or by AC power. A portable curing light system of the invention operates by use of DC batteries, and a chairside non-portable unit is powered by an AC power source.

It is an object of some embodiments of the invention to provide direct beam delivery from a light source to a curing surface where composite materials are to be cured. Direct beam delivery may be provided from a housing where a packaged light source is located to a curing surface with no intermediary light delivery apparatus.

It is an object of some embodiments of the invention to provide a light output apparatus that is flexible so that it may be oriented at any convenient angle. A handpiece may be provided that has a housing with a flexible portion so that it can be angled or bent to a desired orientation for convenient light delivery and use.

It is an object of some embodiments of the invention to provide a curing light system control module with battery power. The control module powers and controls the curing light system so that appropriate light for curing a composite material is provided at a desired light intensity for a desired time duration and indication for battery low.

It is an object of some embodiments of the invention to provide a battery charger that charges one or more batteries which are used to power the light source. When the battery is being charged, the curing light may still be used for treatment because power can be drawn from the charger to power the curing light.

These and other objects, features and advantages of the invention will become apparent to those skilled in the art upon reading the specification and reviewing the appended drawings.

III. BRIEF DESCRIPTION OF THE DRAWINGS

IV. DETAILED DESCRIPTION OF THE PREFERRED EMBODIMENTS

The invention includes various embodiments of a curing light system useful for curing light activated composite materials. The invented curing light system has application in a variety of fields, including but not limited to medicine and dentistry where composite materials with a photoinitiator are used.

Composite materials are applied to a surface and later cured by a variety of methods. One method includes use of a photoinitiator or multiple photoinitiators in the composite material. After the composite material has been placed in a desired location, light of a wavelength that activates the photoinitiator is applied to the composite. The light activates the photoinitiator and initiates curing of the composite material. Although the light used to activate the photoinitiator must be of a wavelength to which a photoinitiator is sensitive, the light can come from a variety of sources, including lasers, light emitting diodes, and conventional lamps.

A. Portable, Battery-Powered Curing Light System

Figure 1A:
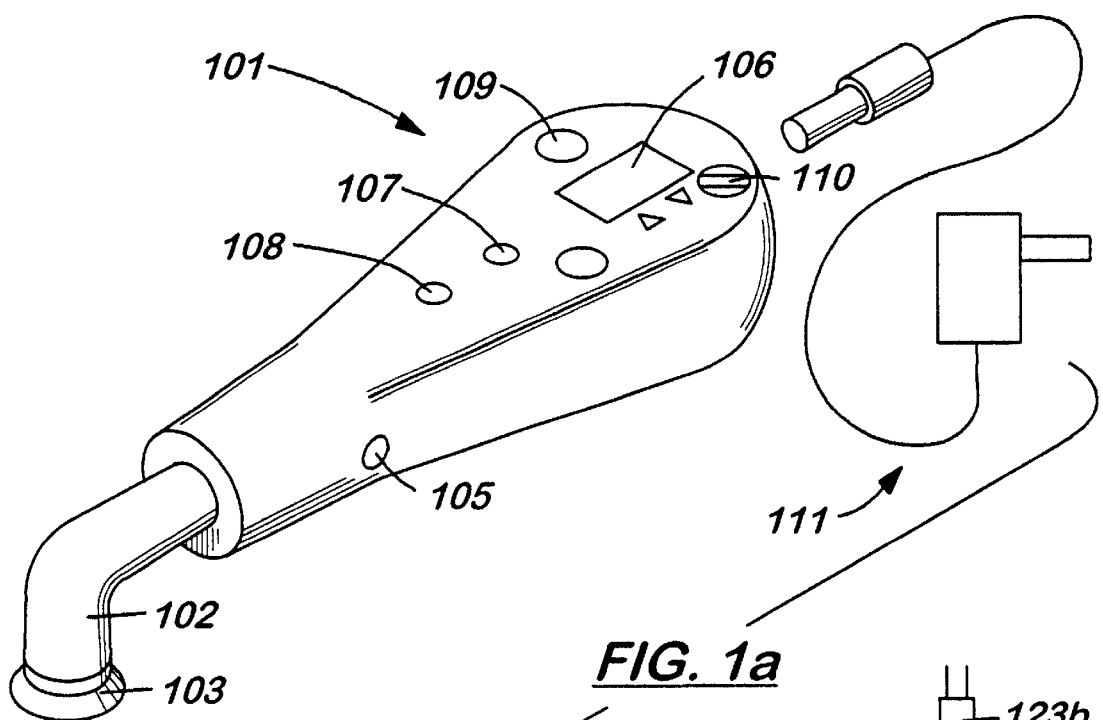
FIG. 1a depicts a battery-operated portable curing light system of the invention.

Referring to FIG. 1a, a preferred portable curing light system 101 of the invention is depicted. The portable curing light system 101 includes a light source module 102 which generates light of a desired wavelength or multiple wavelengths for activating a photoinitiator or multiple photoinitiators and initiating curing of a light activated composite material. The light source module 102 has a light shield 103 for blocking light generated by the curing light system from reaching human eyes and skin. The curing light system 101 includes a housing 104 for containing and protecting electronic circuits and a DC battery pack. A switch 105 such as a button or trigger is located on the housing and may be used to turn the curing light on and off. A timer 106 is provided to control the duration of time that the curing light emits a beam of light. Controls to set the timer are depicted. An audible indicator or beeper 109 is provided to indicate when light emission from the curing light begins and ends. A first LED 107 is located on the housing in a visible location in order to indicate to the user low battery power. A second LED 108 is located on the housing in a visible location in order to indicate to the user that the battering is being charged. A wavelength selector 110 is provided so that the user may select the wavelength of light that he wishes to emit from the curing light, depending on the wavelength sensitivity of the photoinitiator in the composite material that he is using. The user may also select a combination of two or more wavelengths of light to be emitted together.

A separate battery charger module 109 is included in order to receive AC power from a traditional wall socket and provide DC power to the curing light system for both charging the batteries and powering the light source and control circuitry when the batteries if desired.

A unique advantage of the curing light system depicted in FIG. 1a is that all components, including the light source, batteries, control circuitry and user interface are conveniently located in a handpiece. This results in a very portable, yet compact and easy to use curing light system. Only when the batteries are being charged would the user need to have a cord attached to the curing light system or even be in the vicinity of AC power. However, the light system can be operated using power from a battery charger when the battery pack is being charged.

B. Non-Portable Chairside Curing Light System

Figure 1B:
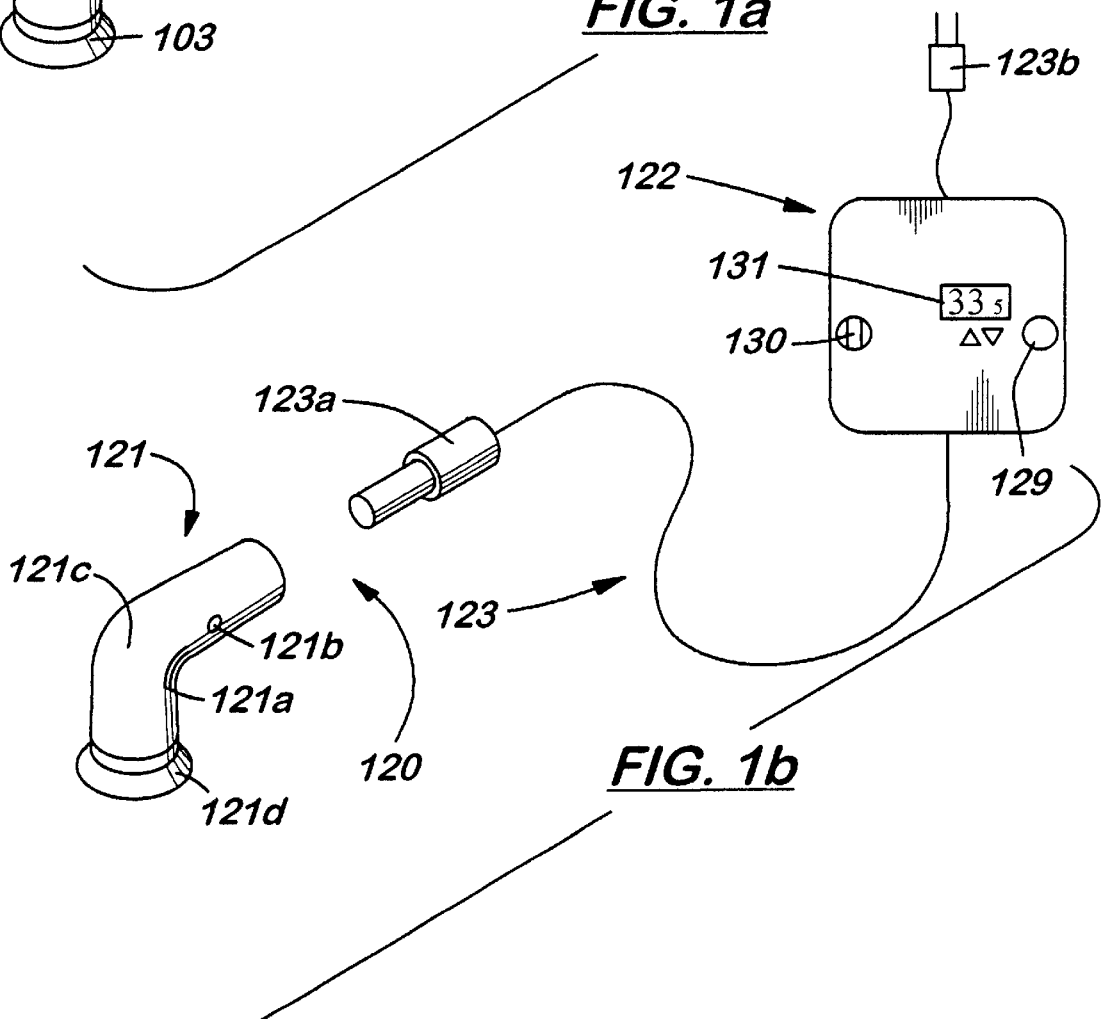
FIG. 1b depicts a non-portable chair-side curing light system of the invention.

Referring to FIG. 1b, a preferred embodiment of a curing light system 120 of the invention is depicted. The curing light system 120 includes a handpiece 121, control circuitry 122 and cabling 123. The handpiece 121 has minimum size, weight and componentry for convenience of use. The handpiece 121 includes a housing 121a, an on/off switch 121b, a light source module 121c, and a light shield 121d. The handpiece 121 receives electrical power from cabling 123 via an electrical connection 123a. Thus, use actuation of the switch 121b allows electrical power to reach the light source module 121c and cause light to be emitted from the handpiece. An audible indicator or beeper 129 is provided to indicate when light emission from the curing light begins and ends. A wavelength selector 110 is provided so that the user may select the wavelength of light that he wishes to emit from the curing light, depending on the wavelength sensitivity of the photoinitiator in the composite material that he is using. The user may also select a combination of two or more wavelengths of light to be emitted together.

All control circuitry 122 is located in a module remote from the handpiece 121. The control module includes a box with a programmable timer 131. A selector for selecting light wavelength 130 may be included. Control circuitry as described elsewhere herein may be included. A plug 123b for connection to an AC power outlet is provided.

This configuration of the invented curing light is intended to be used chairside by a dentist or otherwise used close to an electrical outlet. The curing light system of FIG. 1b minimizes handpiece size and weight by placing control circuitry in a remote module and connecting to that module via a cable. The light source, however, is located in the handpiece so that expensive and heavier fiber optic cabling can be omitted, thus saving expense and weight. If desired, the light source could be located in the remote module 122 and light from the light source could be delivered to the handpiece via fiber optic cabling or a light guide. Such a configuration is not preferred, however.

C. Light Source Module

The light source module, such as the light source modules 102 and 121 above, will typically be an assembly that includes several components. Included components may be a light source module housing, a light shield attachable to the housing, and a light source located within the housing. These components are discussed separately below.

1. Light Source Module Housing

Referring to FIGS. 2a–2d, preferred light source module housings 201 are depicted. The preferred light source module has an exterior housing that performs an encasement function, a protective function, and a maneuverability function, as discussed in greater detail below.

The preferred housing 201 includes four sections connected to each other. These include an electrical connector 202 which can be two-way or multiple pin connector, a flexible section 203, a rigid section 204, and a light shield 205. The light shield 205 has an attachment portion 205a for attaching to the rigid section 204 or other portion of the housing 201. A switch 206 that is only used in the chairside embodiment is provided.

The electrical connector 202 serves to receive electrical power from an electronic control module so that a light source located in the light source module may be powered and generate light.

Figure 2A:
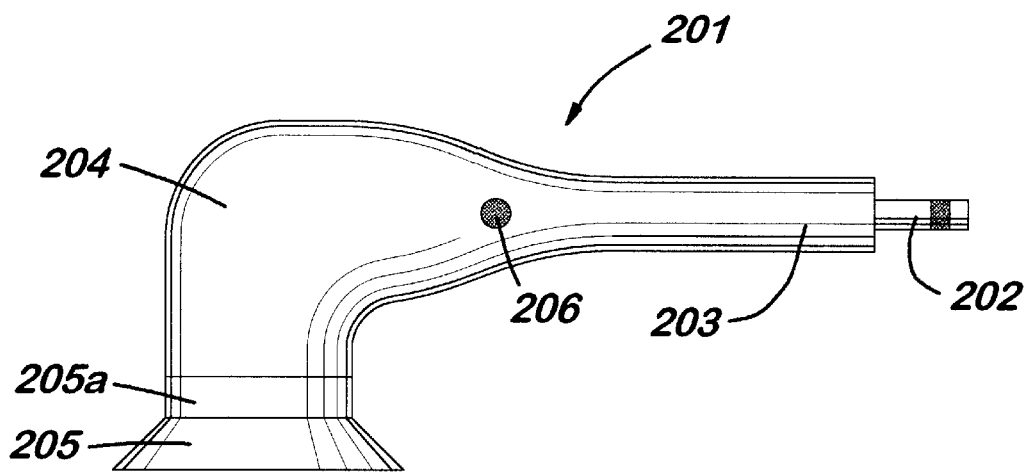
FIGS. 2a–2e depict light modules of the invention.
Figure 2B:
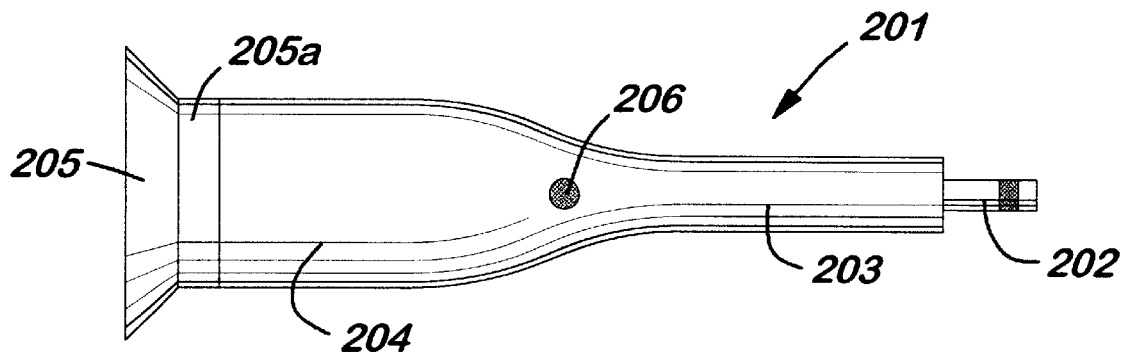
Figure 2C:
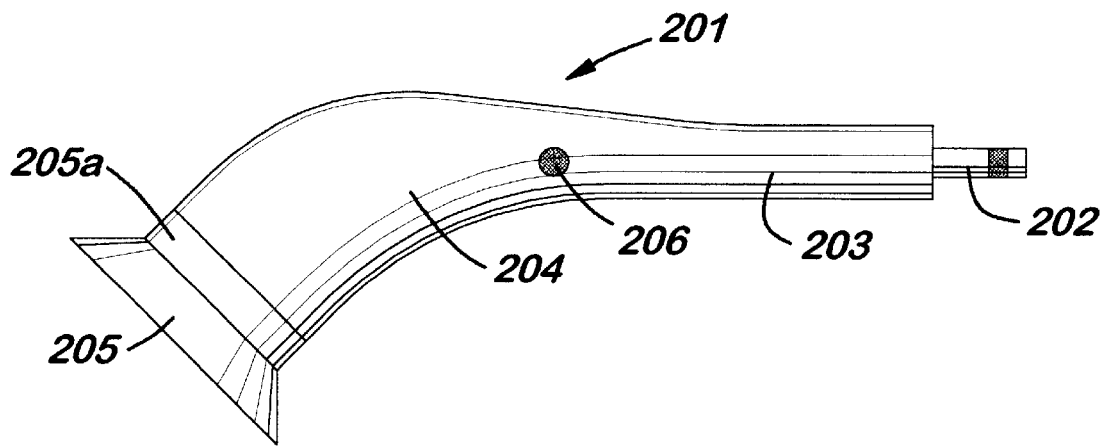

The rigid section 204 preferably will encase a light source. The rigid section 204 may be oriented at a 90 degree angle to the longitudinal axis of the remainder of the light source module housing (as in FIG. 2a), at 180 degrees (FIG. 2b), or 45 degrees (FIG. 2c).

Figure 2D:
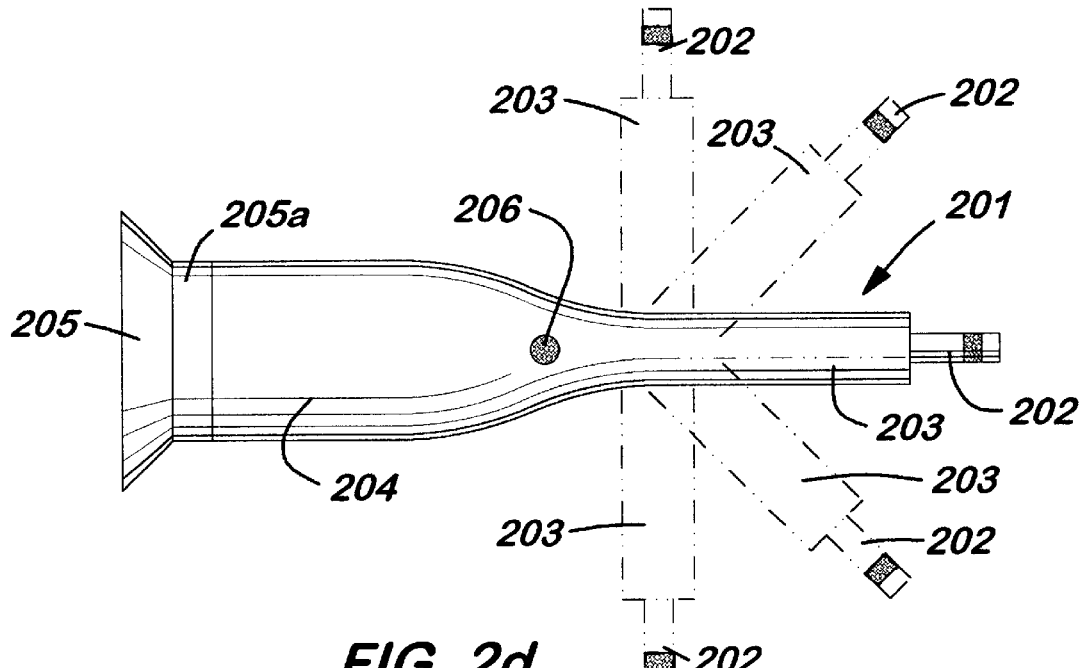

Flexible section 203 is flexible in order to facilitate bending. The flexible section 203 has an exterior of flexible tubing and a bendable wire located on its interior. The flexible tubing and bendable wire preferably accommodate repeated bending from −90 degrees to +90 degrees angles as depicted in FIG. 2d.

Figure 2E:
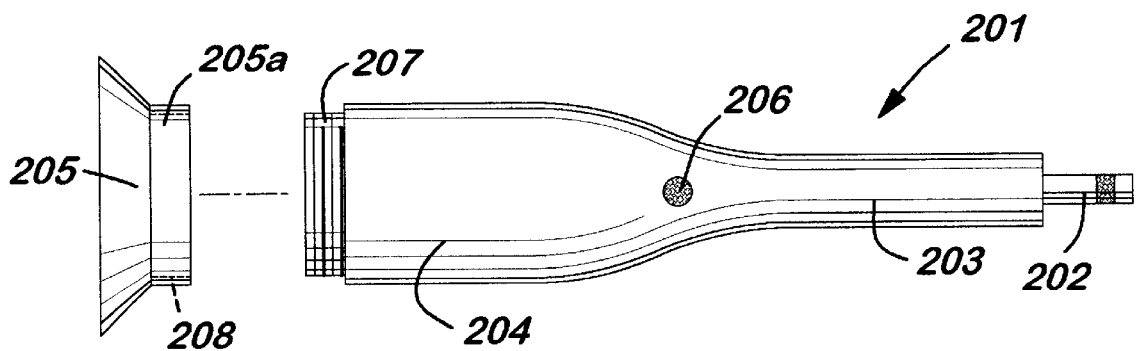

Referring to FIG. 2e, a light source housing is depicted with the preferred light shield 205 removed. It can be seen that the rigid section 204 has an end 207 shaped to accommodate fitting with a receptacle 208 on the attachment portion 205a of the light shield 205. The light shield can be attached by other known means, such as frictional engagement, adhesion, welding, threads, and use of mechanical fasteners such as screws or pins. In other embodiments of the invention, the light shield might be integral with the rigid section 204, it might be replaced with a light delivery device such as fiber optic cable or a light guide, or it might be omitted.

Figure 2F:
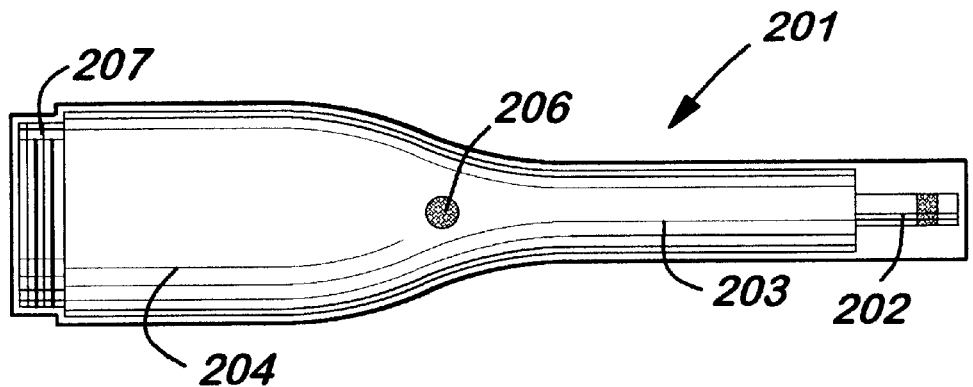
FIG. 2f depicts an infection control shield of the invention.

Referring to FIG. 2f, an optional infection control shield 210 is provided on a light source 201 (as already discussed). The infection control shield 210 is preferably thin and flexible plastic, rubber, polymer or paper material that fully encases the light source in order to prevent physical contact of the light source with a patient. If desired, the infection control shield 201 may be a rigid or semi-rigid material such as plastic. The infection control shield 210 serves as a sterile glove for the light source.

Before the curing light is used to cure composite materials, an infection control shield 210 may be installed over the light source. After a medical provider has finished using the light source to cure composite materials, the infection control shield may be removed and discarded. A new infection control shield or sterilized shield may be installed before the curing light is used on another patient. In this way the curing light is always kept clean and each patient will enjoy the benefits and protection of a new and sterile infection control shield. In this manner, bacterial communication between patients can be eliminated and possibility of transmission of infectious disease can be drastically reduced.

2. Light Shield

Figure 3A:
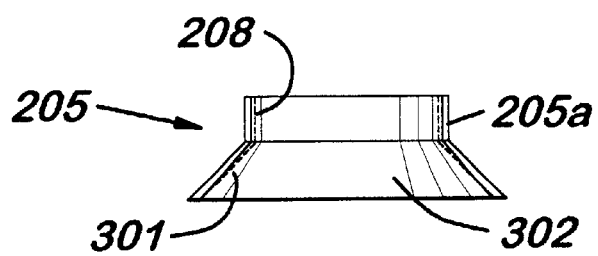
FIGS. 3a & 3b depict a light shield of the invention.
Figure 3B:
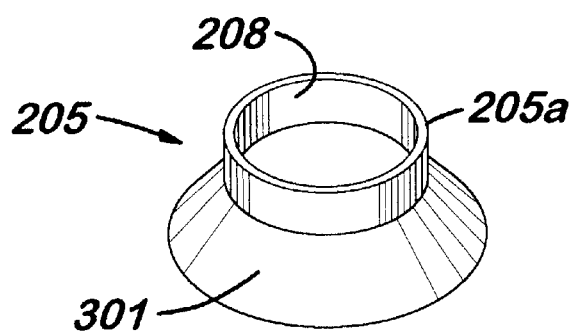

Referring to FIGS. 3a and 3b, the light shield 205 is depicted. It includes an attachment portion 205a which may include attachment means such as a receptacle or fitting 208 for attachment to a curing light. It also includes a bell or conical portion 301 which serves to shield light emitted from the curing light system without interfering with its path. The bell 301 may be frusto-conical in shape with an interior bore 302 through which light is emitted by the light source. The light shield 205 serves to block the light from laser or light emitting diodes from striking the eyes or skin of a user of the curing light. The light shield 205 may be constructed of any material has a low transmission percentage for the wavelength of light emitted by the curing light source.

3. Light Module a. Example of Light Module Assemblies

Figure 4A:
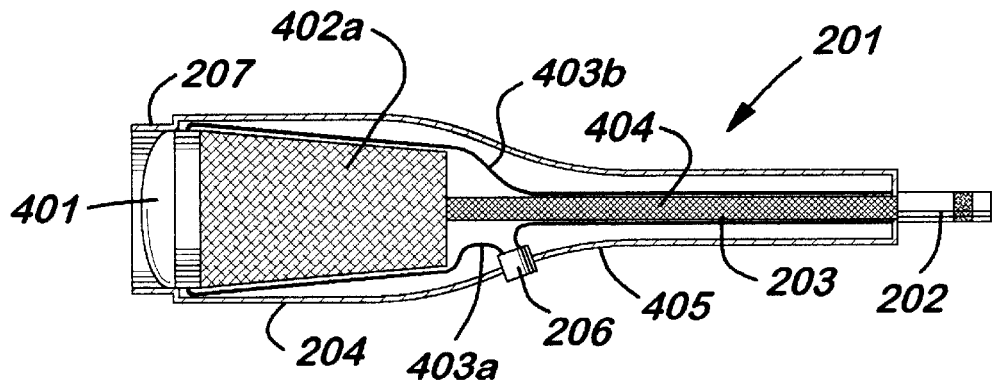
FIGS. 4a & 4b depict cross sectional views of the interior of different embodiments of the light module.
Figure 4B:
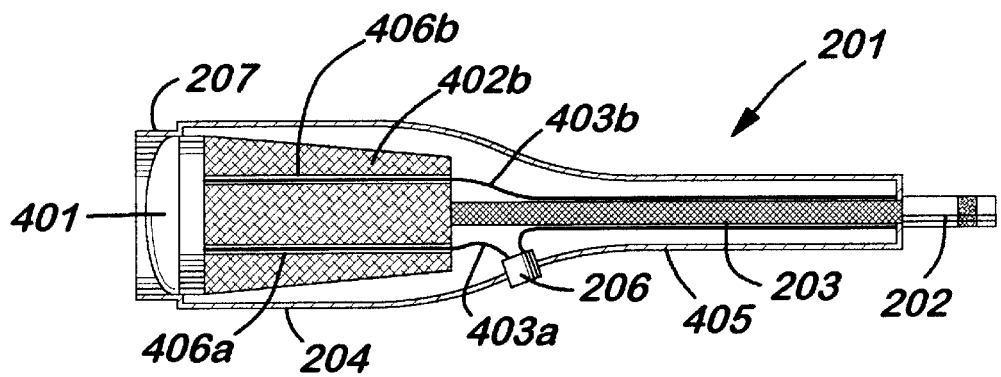

Referring to FIGS. 4a and 4b, cross sectional views of two different light module assemblies in a housing are depicted. The light module assemblies include a housing 201 as described previously.

A light source 401 is located adjacent a heat sink 402a or 402b in FIG. 4a and 4b, respectively. Flexible wires 403a and 403b are used to connect the light source 401 to an electrical connector 202. A bendable wire 404 inside a flexible tube 405 allows section 203 to be bendable from −90 degrees to +90 degrees. An electrical switch 206 is provided only for the chairside embodiment.

Electrical connector 202 can be any two-way or multiple pin electrical male or female connector. Flexible tube 405 can be any flexible plastic, rubber, or metal materials. Rigid section 204 can any solid plastic or metal materials. Bendable wire 404 can be any appropriate gage of solid wire that accommodates the desired bending. Electrical wire 403a and 403b can be any flexible electrical wires. The total number of wires like 403a and 403b for electrical connections depends on number of chips with different wavelength in light source 401. Basically, chip with one wavelength requires an individual electrical connection.

The heat sinks 402a and 402b are used to help to dissipate the heat generated by the light source 401. Preferably the heat sink 402a and 402b will have a greater size than the size of the light source 401, and preferably the light source 401 will be mounted adjacent to and in physical contact with the heat sink 402a and 402b for most efficient heat dissipation.

Two different types of heat sinks 402a and 402b are depicted. Heat sink 402a has a solid configuration and is used when the light source 401 relies on electrodes which travel along the sides of the heat sink 402a and connect to the sides of the light source 401. The alternative heat sink 402b includes two channels 406a and 406b or multiple channels depending the numbers of chips with different wavelength in the light module. Each chip with individual wavelength requires individual electrical connection and individual channel in the heat sin. The electrodes through channels in heat sink may be placed in order to reach the bottom of the light source 401 adjacent the heat sink. The channels 406a and 406b may be drilled or otherwise formed in the heat sink.

b. Light Sources

As desired in various embodiments of the invention, the light source may be (a) a single LED chip, (b) an array of LED chips, (c) a single diode laser chip, or (d) an array of diode laser chips. The wavelength of light emitted from the LED or diode laser chips can be any desired wavelength or combination of different wavelength, depending on the sensitivity of the photoinitiator(s) in the composite material to be cured.

1.) LED Types

Figure 5A:
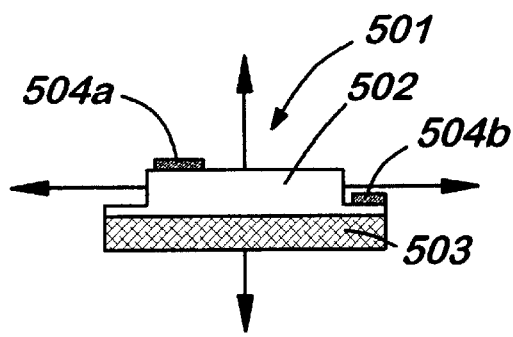
FIGS. 5a & 5b depict two different LED types that may be used in the invention.
Figure 5B:
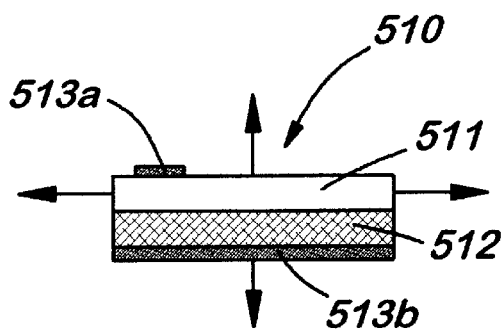

Two types of LED chips that may be used in the invention are depicted in FIGS. 5a and 5b. Referring to FIG. 5a, an LED 501 is depicted in which the LED structure 502 has been grown on top of or on one side of an insulating substrate 503. Electrodes 504a and 504b are provided to power the LED. In such a structure, all electrodes will be located on the top surface of the LED. Light is emitted from both the sides and the top of the LED as depicted by the arrows in the Figure. Usable light can also be emitted from the bottom of the LED if the insulating substrate is transparent to the light emitted.

Another type of LED chip 510 that may be used in the invention is depicted in FIG. 5b. The LED 510 has LED structure 511 grown on a conductive substrate 512. Electrodes 513a and 513b are provided to power the LED. Light is emitted from the sides, top, and bottom of the LED as depicted by the arrows in the Figure. The electrodes 513a and 513b are located on the top and bottom of the chip, respectively.

2.) Semiconductor Diode Laser Types

Figure 6A:
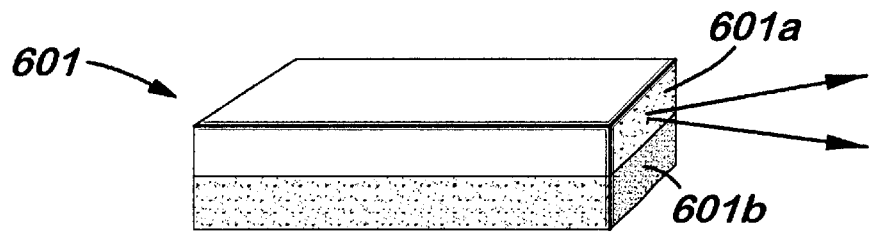
FIGS. 6a–6d depict different types of laser chips that may be used in the invention.
Figure 6B:
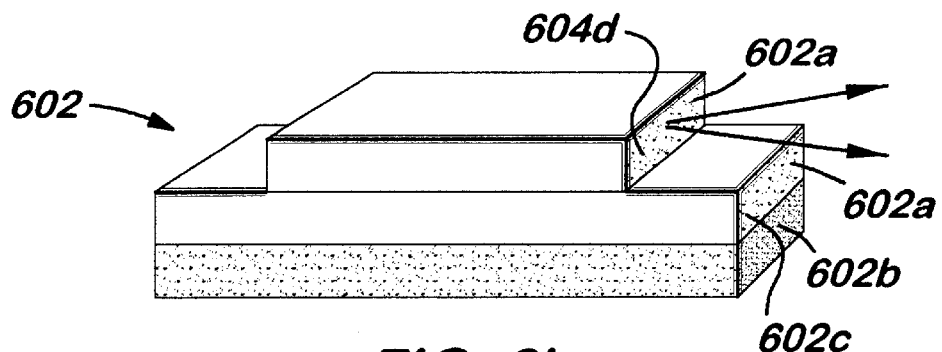
Figure 6C:
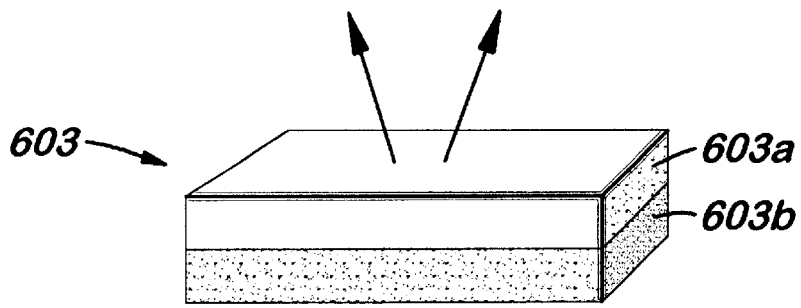
Figure 6D:
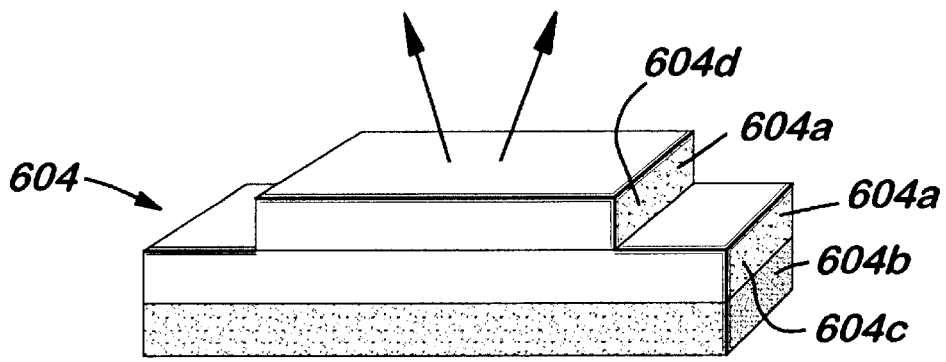

Instead of LED's, semiconductor diode lasers may be used as the light source in the invention. Examples of semiconductor diode lasers are depicted in FIGS. 6a–6d. Semiconductor diode lasers are generally made using the same or similar materials as LED's, but the structure of a semiconductor diode laser differs from that of an LED. Semiconductor diode lasers include edge emitting diode lasers as depicted in FIGS. 6a and 6b, and surface emitting diode lasers as depicted in FIGS. 6c and 6d.

Referring to FIG. 6a, edge emitting diode lasers 601 is depicted. It includes laser structure 601a grown on a conductive substrate 601b. Light is emitted from the sides of the laser structure 601a. Preferably, a reflective coating will be placed on one side of the laser structure so that most light is emitted from only one side of the chip as indicated by the arrows.

Referring to FIG. 6b, another edge emitting diode laser 602 is depicted. It includes laser structure 602a grown on an insulating substrate 602b. A first layer 602c of laser structure on the substrate acts as an electrical contact and will not emit light. Light is only emitted from the sides of a second layer 602d of laser structure.

Referring to FIG. 6c, a surface emitting diode laser 603 is depicted. Laser structure 603a has been grown on a conductive substrate 603b and light is emitted from the surface of the chip as indicated by the arrows.

Referring to FIG. 6d, a surface emitting diode laser 604 is depicted. It includes laser structure 604a grown on an insulating substrate 604b. A first layer 604c of laser structure on the substrate acts as an electrical contact and will not emit light. Light is only emitted from the surface of a second layer 604d of laser structure.

Similar to LED's, the electrodes for laser diode chips are grown on the top and bottom for a conductive substrate, and on the top and side for an insulated substrate.

c. Light Source Assemblies

FIGS. 7a, 7b, 8a, 8b, 9a, 9b, 10a, 10b, 11a, 11b, 12a, 12b, 13a and 13b depict various light source assemblies that may be used in the curing light of the invention. The light source assembly preferred in the invention generally includes at least one LED or laser diode chip located on a heat sink, such as those depicted in the Figures.

1.) Single LED Chip

Figure 7A:
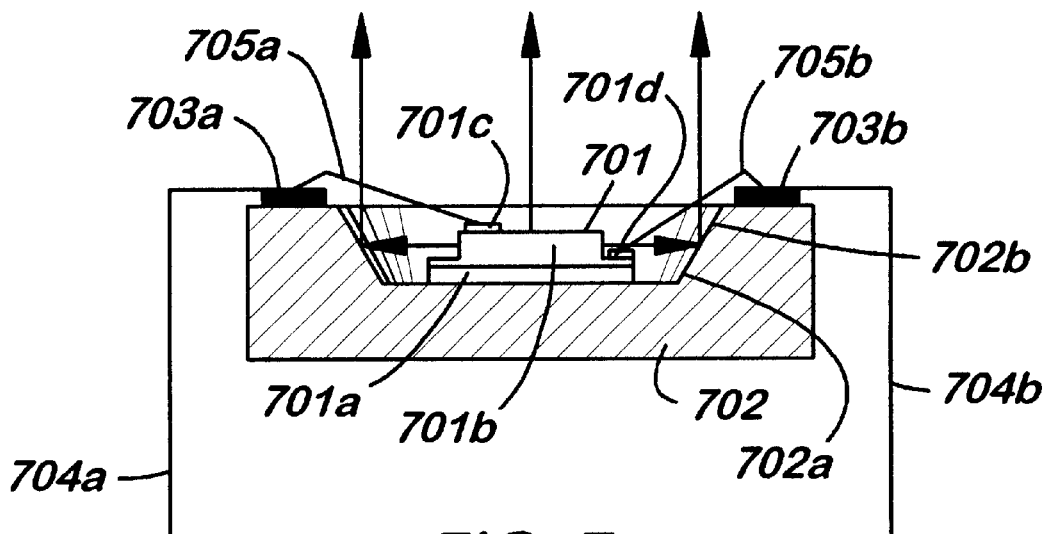
FIGS. 7a & 7b depict a light source that uses a single light emitting diode with an insulating substrate.

Referring to FIG. 7a, a side view of a light source assembly is provided. The light source assembly includes a single LED chip 701 located on a heat sink 702. The LED chip depicted has an insulating substrate 701a and LED structure 701b. Electrodes 701c and 701d are located on the LED chip. Intermediary islands 703a and 703b are located on the heat sink 702 for ease of electrical connection to electrodes 701c and 701d with wires 705a, 705b, 704a and 704b. 703a and 703b are insulated from heat sink and may not be used if proper wire bonding technique is used.

The LED chip 701 is located in a circular well 702a of the heat sink 702. The circular well 702a is formed with sides or walls 702b at about a 45 degree angle or other desired angle so that light emitted from the side of the chip will be reflected from the walls of the well in a desired direction as indicated by arrows in the figure. This allows the highest possible light intensity to be obtained using a chip of given size.

Figure 7B:
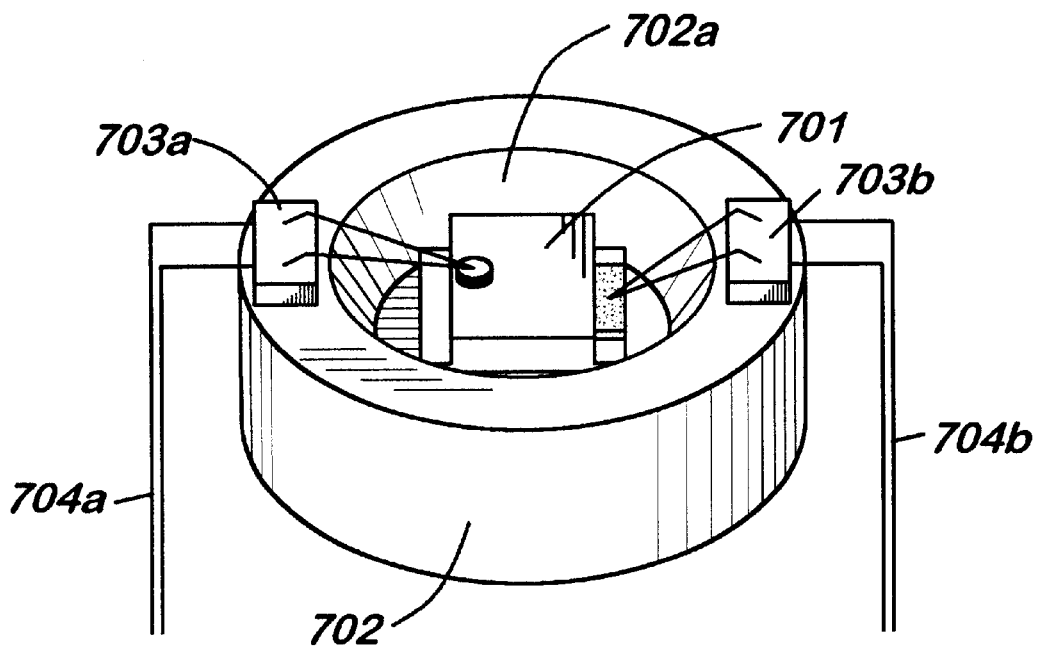

FIG. 7b depicts a perspective view of the assembly of FIG. 7a.

Figure 8A:
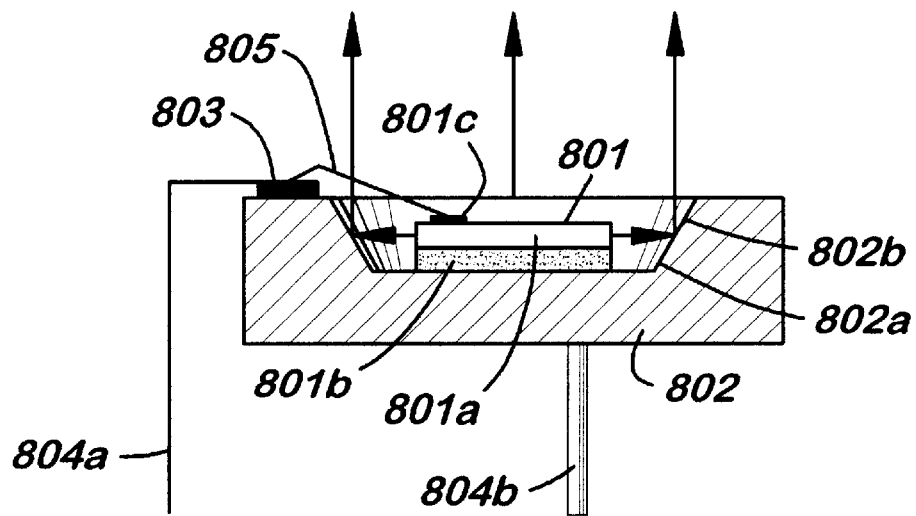
FIGS. 8a & 8b depict a light source that uses a single light emitting diode with a conductive substrate.

Referring to FIG. 8a, a side view of another light source assembly is provided. An LED chip 801 is located in a circular well 802a of the heat sink 802. The circular well 802a is formed with sides or walls 802b at about a 45 degree angle or other desired angle so that light emitted from the side of the chip will be reflected from the walls of the well in a desired direction as indicated by arrows in the figure. This allows the highest possible light intensity to be obtained using a chip of given size. The LED chip 801 depicted has an LED structure 801a, a conductive substrate 801b, and electrode 801c. An electrode 804a is connected to an electrodes of the LED chip through an intermediary island 803 which is insulated from heat sink. Another electrode 804b is provided on the heat sink 802 for electrical connection.

Figure 8B:
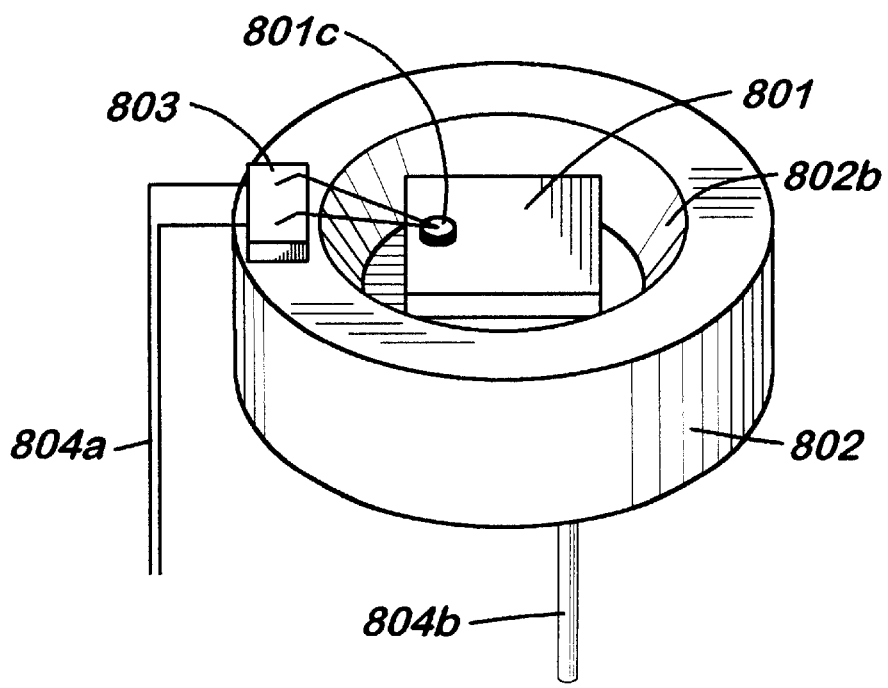

FIG. 8b depicts a perspective view of the assembly of FIG. 8a.

2.) LED Chip Array

When a high intensity light source or multiple wavelengths are desired, chips may be arranged into an array to provide the desired intensity.

Figure 9A:
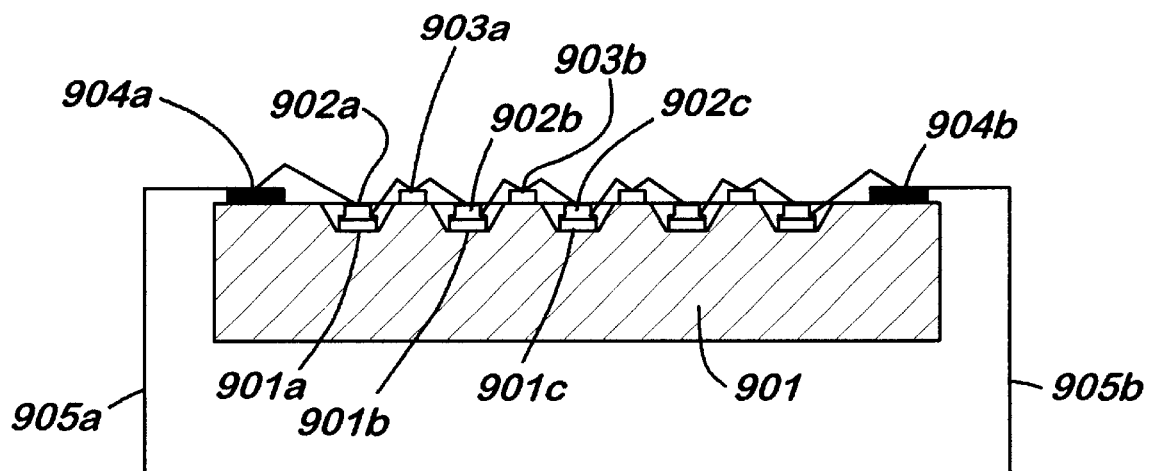
FIGS. 9a & 9b depict a light source that use an array of light emitting diodes with intermediary islands and an insulating substrate.

Referring to FIG. 9a, a side view of another light source assembly is provided. The assembly includes a heat sink 901. The heat sink 901 includes an array of wells 901a, 901b, 901c, etc. in which an array of LED chips 902a, 902b, 902c, etc. is located. Intermediary islands 903a, 903b, etc. are provided to facilitate electrical connection. 903a, 903b, etc are insulated from heat sink and may not be used if proper wire bonding technique is used. The LED chips depicted use an insulating substrate and electrodes on top of the chips. The connection of the LED chips can be serial, parallel, or combination of serial and parallel depending application requirement. Preferably, the electrodes used to connect the LED chips to each other will be extruded from the LED chips and will receive power through intermediate islands 904a and 904b that are connected to electrodes 905a and 905b.

Figure 9B:
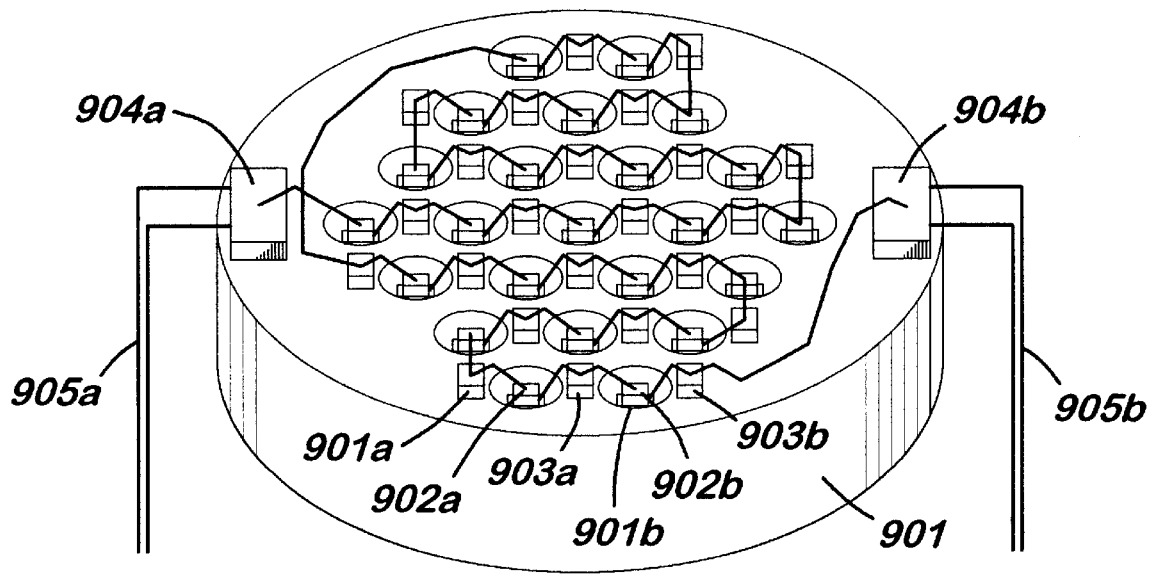

A top view of an LED array is depicted in FIG. 9b. The arrangement of chips on top of a heat sink can be in any pattern or compact configuration and can be in wells or simply located on the heat sink surface.

Figure 10A:
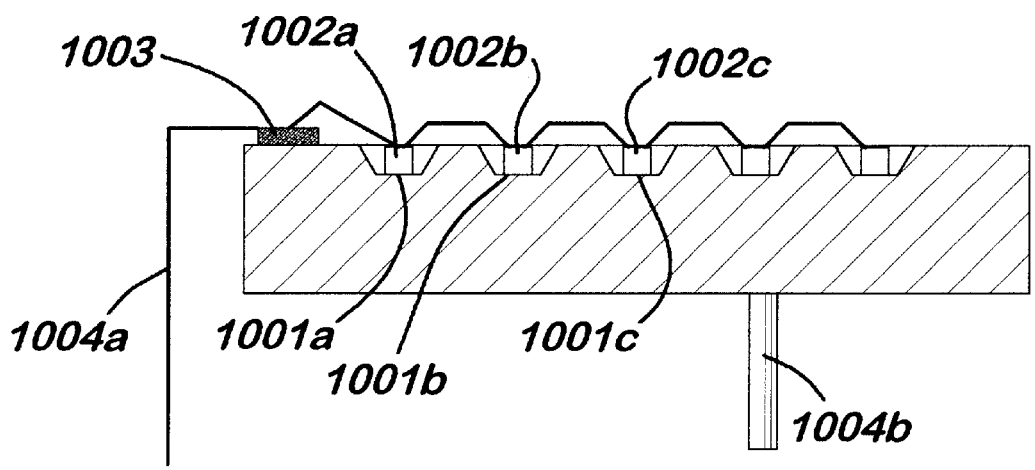
FIGS. 10a & 10b depict a light source that uses an array of light emitting diodes with a conductive substrate.

Referring to FIG. 10a, a side view of another light source assembly is provided. The light source assembly includes an array of LED chips 1002*a*, 1002*b*, 1002*c* etc. located in wells 1001*a*, 1001*b*, 1002*c*, etc. on a heat sink 1001. The LED chips depicted have LED structure on a conductive substrate and heat sink acts as one electrode, therefore, one electrode 1004*a* is connected to the LED chip array through intermediate island 1003 which is insulated from heat sink and anther electrode 1004*b* is provided on the heat sink. The connection of the LED chips can be serial, parallel, or combination of serial and parallel.

Figure 10B:
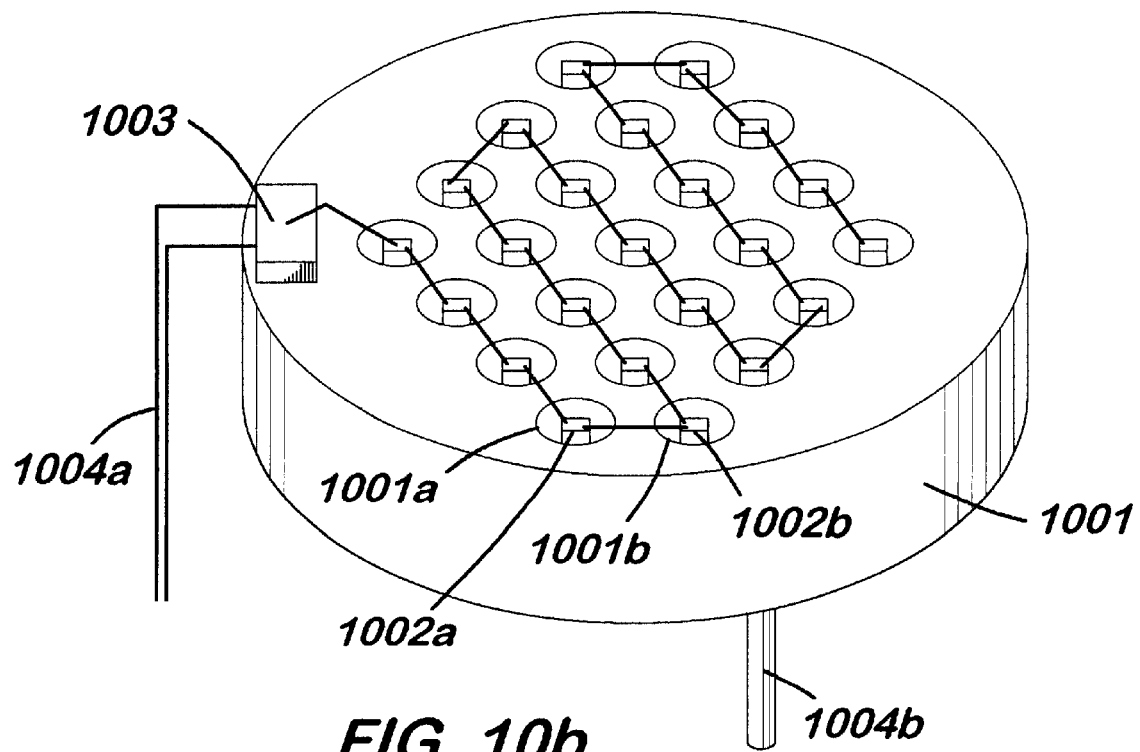

FIG. 10*b* depicts a perspective view of the assembly of FIG. 10*a*.

Figure 11A:
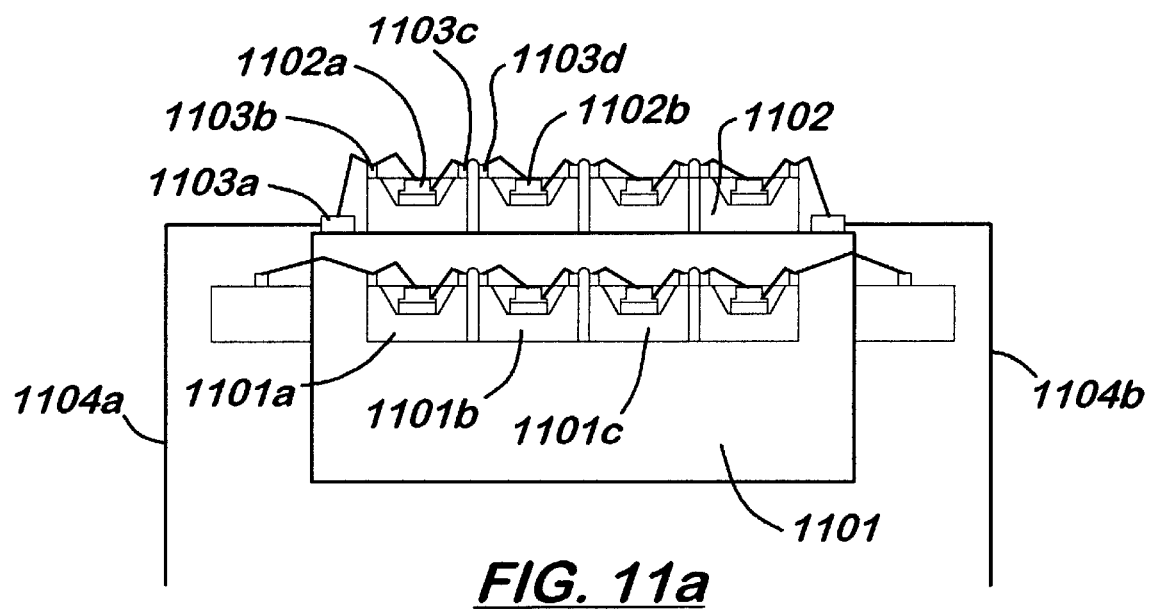
FIGS. 11a & 11b depict a light source that uses using an N×M array of pre-packaged LED's on an insulating substrate and using intermediary islands.
Figure 11B:
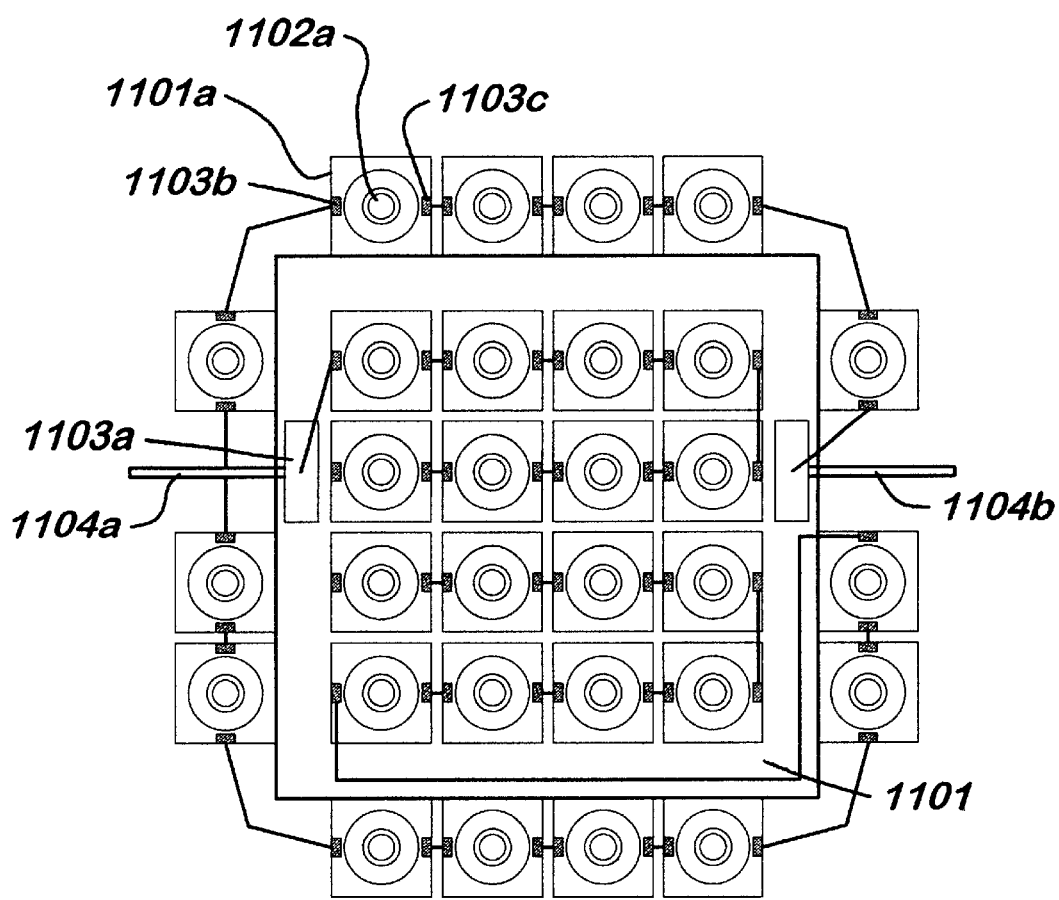

Referring FIGS. 11*a* and 11*b*, an array of pre-mounted LED's on a heat sink is depicted. A heat sink 1101 has pre-packaged or pre-mounted LED's 1101*a*, 1101*b*, 1101*c*, etc. located on it. The LED's have been located both on one face of the heat sink and around the periphery of the heat sink. The periphery of the heat sink is depicted as being square, although it could be any desired shape including round, rectangular, polygonal, or another shape. The LED's are mounted both on the face of the heat sink and around the periphery of the face of the heat sink to increase light power or give an choice of different wavelength. Using all available area to mount LED's can increase the total number of LED's and result in a light source that produces more light per unit area for a more powerful light or selection of different wavelength.

The pre-packaged LED's 1101*a*, 1101*b*, 1101*c*, etc. have an LED chip 1102*a*, 1102*b*, 1102*c*, etc., respectively, each in their own well on their own small heat sink. The individual heat sinks are mounted on the primary heat sink 1101 so that heat generated by the pre-packaged LED's is transferred through the individual heat sinks to the main heat sink 1101. The pre-packaged LED's can be connected to each other by wiring in any desired format (serial, parallel, or a combination of parallel and serial). Intermediary islands 1103*a*, 1103*b*, 1103*c*, etc., may be provided for ease of electrical connection to electrodes 1104*a* and 1104*b*. Multiple electrodes may be used when chips with different wavelength are arranged in the array. Chips with one wavelength require individual electrode for the group.

3.) Single Laser Chip

Instead of LED's, it may be desired to use semiconductor laser chips in the light source assembly. As explained previously, two types of semiconductor laser chips that may be used are surface emitting chips and edge emitting chips. Depending on light intensity requirements, semiconductor laser chips may be used with a single laser chips or an array of laser chips in the light source.

Figure 12A:
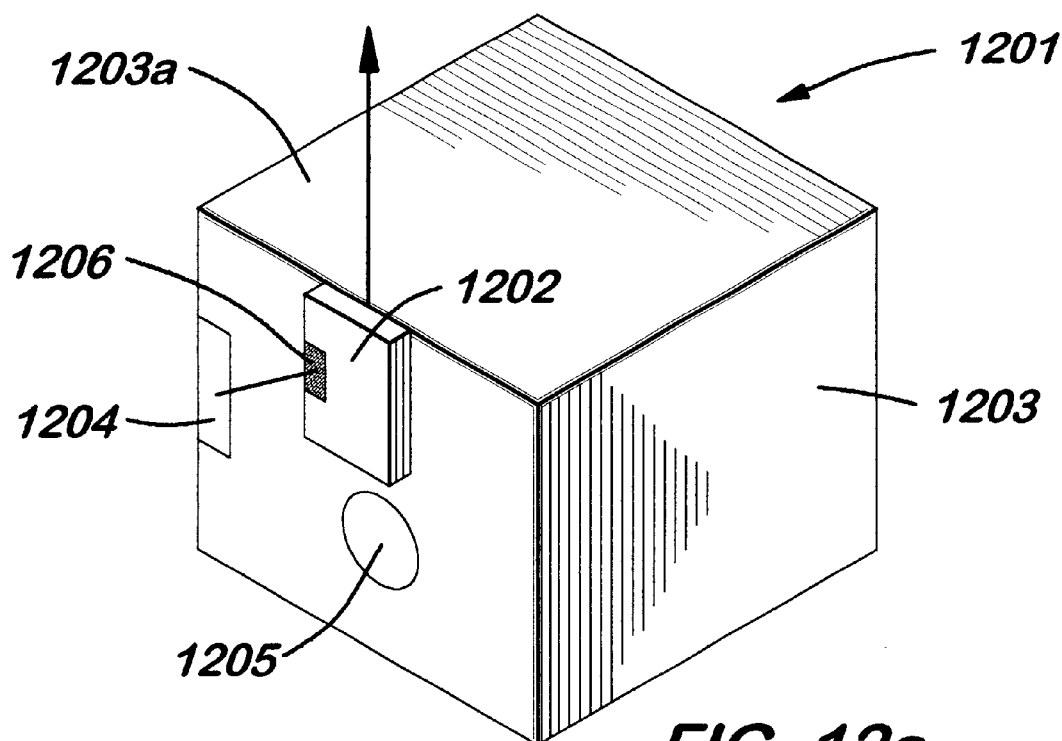
FIG. 12a depicts an edge emitting laser diode chip mounted on a heat sink.

Referring to FIG. 12*a*, a light source assembly 1201 is depicted that includes a single edge emitting semiconductor laser chip 1202 located on a heat sink 1203. The laser chip 1202 emits light from an edge as indicated by the arrow. The chip is therefore located at the edge of one face 1203*a* of the heat sink 1203. The chip 1202 has an electrode 1206 connected to an intermediary island 1204 which is insulated from heat sink 1203. As the chip 1202 has a conductive substrate, the heat sink 1203 serves as the other electrode. A chip with an insulating substrate could be used with only a minor difference in electrical connection. There is a hole 1205 in the heat sink for attachment to another heat sink as desired.

Figure 12B:
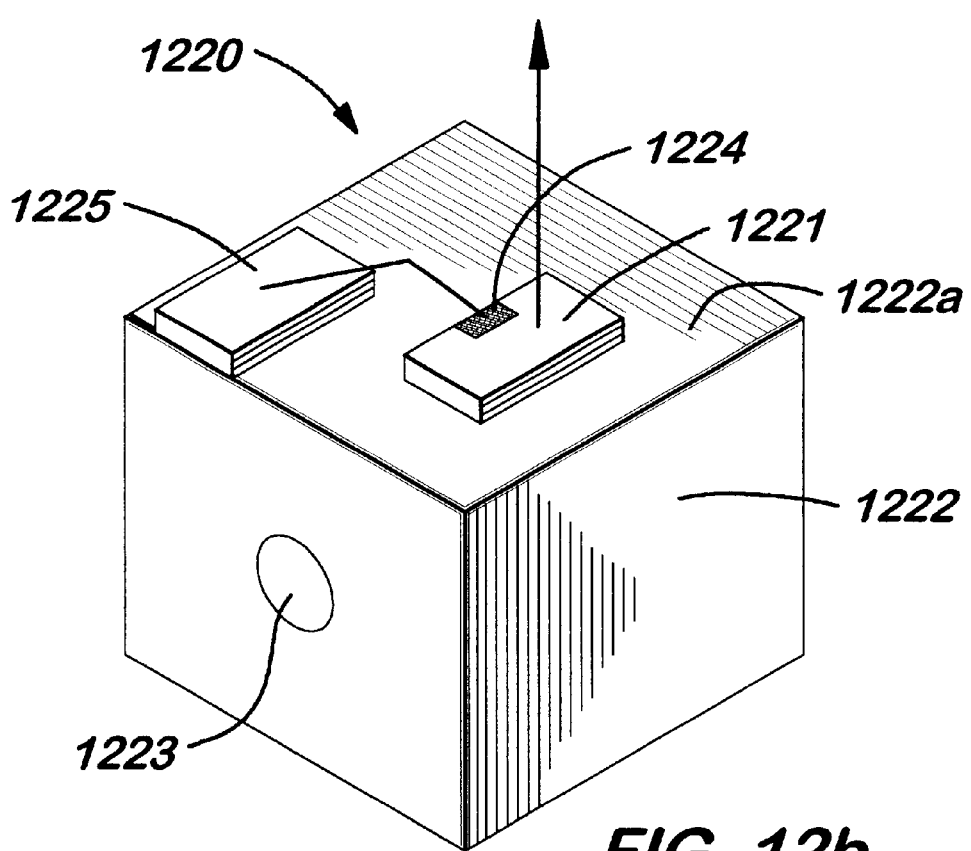
FIG. 12b depicts a surface emitting laser diode chip mounted on a heat sink.

Referring to FIG. 12*b*, a light source assembly is depicted that includes a single surface emitting laser chip 1221 located on a heat sink 1222. The laser chip 1221 emits light from a surface as indicated by the arrow. The chip is therefore located on a face 1222*a* of the heat sink 1222. The chip 1221 has an electrode 1224 connected to an intermediary island 1225 which is insulated from heat sink. As the chip 1221 has a conductive substrate, the heat sink 1222 serves as the other electrode. A chip with an insulating substrate could be used with only a minor difference in electrical connection. There is a hole 1223 in the heat sink for attachment to another heat sink as desired.

4.) Laser Chip Array

Figure 13A:
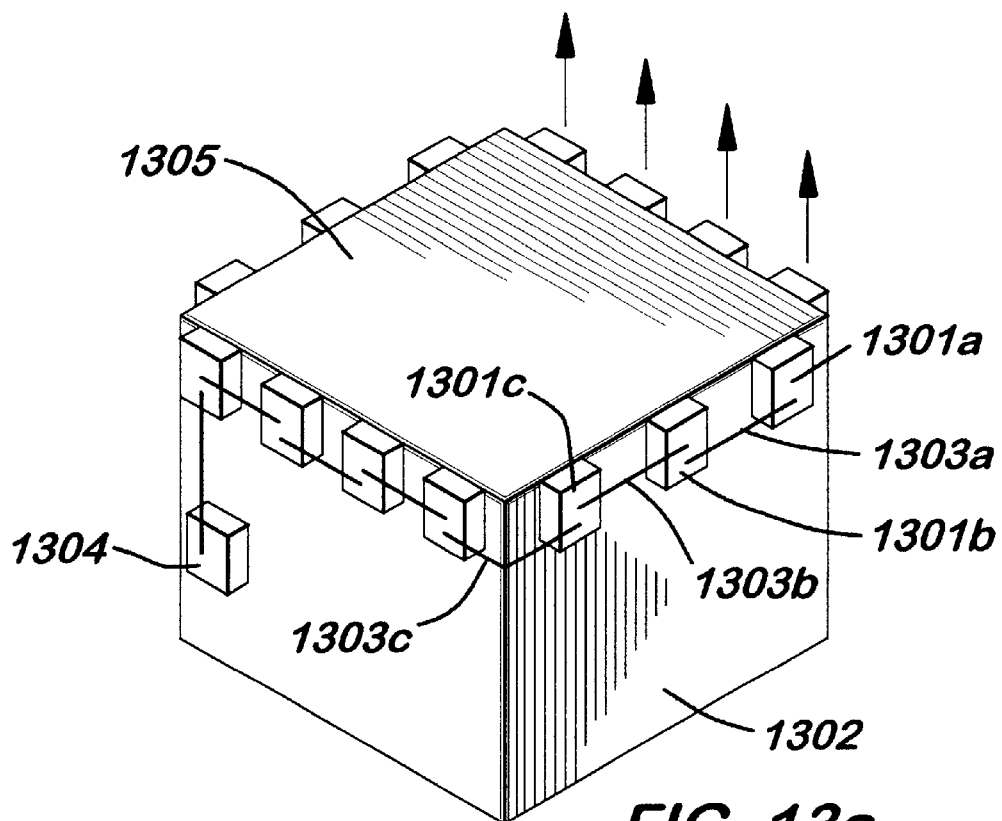
FIG. 13a depicts an array of edge emitting diode laser chip s mounted about the circumference of one end of a heat sink.

Referring to FIG. 13*a*, a light source is depicted that includes an array of edge emitting semiconductor laser chips 1301*a*, 1301*b*, 1301*c*, etc., located on a heat sink 1302. The chips receive power through electrical connection 1303*a*, 1303*b*, 1303*c*, etc., through intermediary island 1304 which is insulated from heat sink. Heat sink 1302 also acts as one electrode connection for power supply. The chips are located along the edge of one face 1305 of the heat sink 1302. As depicted, the chips emit light in a direction generally perpendicular to that face 1305 as indicated by arrows in the figure. The laser chips can be any type described herein.

Figure 13B:
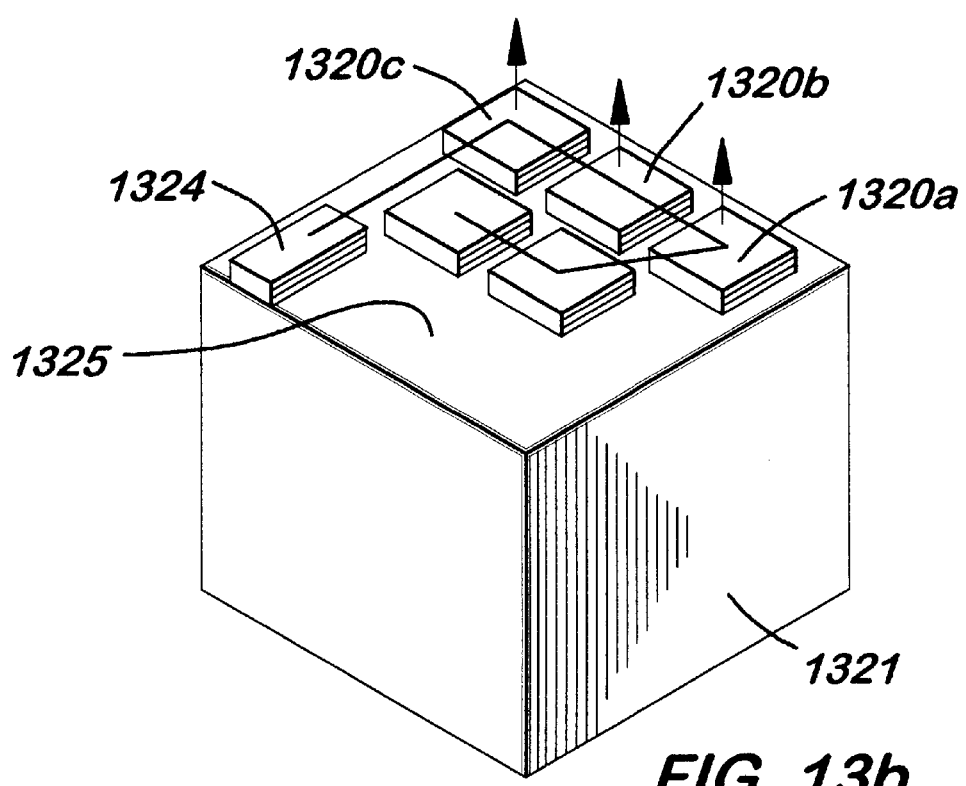
FIG. 13b depicts an array of surface emitting diode laser chips located on one face of a heat sink.

Referring to FIG. 13*b*, a light source is depicted that includes a heat sink 1321 with a face 1325 and an intermediary island 1324 which is insulated from heat sink for electrical connection. Heat sink also acts as one electrode connection for power supply. An array of surface emitting diode laser chips 1320*a*, 1320*b*, 1320*c*, etc. is located on one face 1325 of the heat sink 1321. The chips emit light from one surface in a direction generally perpendicular to the face on which they are located, as indicated by arrows in the figure. The laser chips can be any types as described herein.

The LED or laser chips used in the invention can be any desired size depending on the light intensity required for the application. The material of the heat sink can be any material or combination of materials with high heat conductance. The size of the heat sink will vary with size of the chip(s) used. The shape of the heat sink is not considered important and can be modified as appropriate for the application. The chips may be arranged into any desired array, closely packed, widely spaced, or in an N×M array where N and M are integers. The electrical connection for the chips can be parallel, serial or a combination of parallel and serial, as desired.

d. Producing Light of Several Wavelengths

Most composite materials contain a single photoinitiator and are therefore sensitive to a single wavelength of light. Composite materials from different manufacturers use different photoinitiators and that are sensitive to light of different wavelengths. It is therefore desirable to provide a curing light that can produce light of several wavelengths so that it may be used to cure a variety of different composite materials.

In the various embodiments of the invention, LED's or laser diode chips capable of producing light of different wavelengths can be used in combination on a single heat sink. Consequently, the curing light will emit light of different wavelengths so that the light can cure several different composite materials that have photoinitiators sensitive to light of different wavelengths. If the curing light is used to produce a wavelength of light that is not visible to the human eye, then a visible wavelength can be added to aid in use of the curing light. The light source can be constructed to emit light of 1 to N wavelengths, where N is an integer. Such a light source may require a large number of LED's or laser diode chips, such as that depicted in FIGS. 11*a* and 11*b*. A control switch such as 110 in FIG. 1*a* or 130 in FIG. 1*b* may be provided on the curing light so that the user may select the wavelength of light to be emitted, and the electronic control can accommodate this wavelength selection feature.

e. Light Source Encasement

Once a light source has been constructed, one or more LED's or laser diode chips are mounted on a heat sink. In order to protect the heat sink and LED's or laser diode chips, an appropriate encasement may be used. The encasement should seal and protect the light source, but permit light to exit the light source and travel to a curing surface where a composite material is to be cured. The encasement should protect the chip(s) and electrical components of the light source from mechanical, chemical and electrical damage due to the environment in which they are used. The encasement will preferably be sealed from exposure to air and moisture with only the electrodes exposed to the exterior of the encasement. The encasement may be of any shape suitable for the application. The encasement may also serve as a handle for applying curing light to a curing surface. In some preferred embodiments of the invention, the light source encasement will be within or a part of rigid portion depicted in FIGS. 2a–2e and FIGS. 4a and 4b and discussed in the text corresponding to those figures. The material below provides details on preferred constructions of light source encasements and in particular the light exit. Some embodiments of the encasement will have structure intended to modify the optical qualities of light emitted from the light source.

Figure 14A:
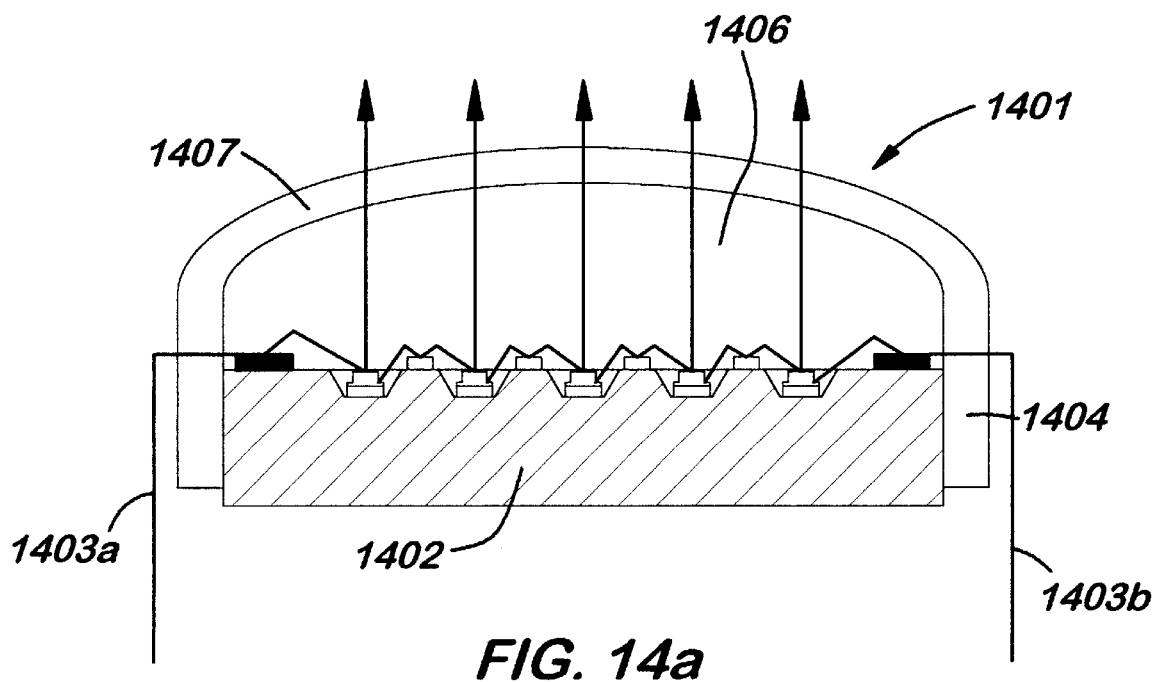
FIG. 14a & 14b depict a portion of a housing of the invention that includes a focus dome for focusing light emitted by the light source.

Referring to FIG. 14a, a light source encasement 1401 is depicted. A light source 1402 is located in the encasement. Light source 1402 may be a single LED chip or an array of LED chips with an insulating substrate. An LED array light source is depicted as an example light source for the purposes of discussing FIG. 14a, but any appropriate light source could be employed. The light source encasement 1401 includes a cylindrical portion, tubular portion or body 1404. The body 1404 has a hollow interior bore 1405 in which the heat sink of the light source 1402 is firmly mounted. The body 1404 serves to contain and protect the light source. The body 1402 is insulated with heat sink of light source 1402. The body 1404 is preferably made from plastic for light weight, durability and low cost, but may be made of metal, fiber-reinforced composite or other material for superior aesthetics or a look and feel of quality. At the distal end of the bore 1405, there is a light exit 1406 through which light may pass that has been emitted from the LED(s) in the light source (see arrows in the Figure). It is intended that light will be generated by the light source, pass through the light exit, and travel to a curing surface in order to initiate curing of a photosensitive composite material. As depicted, the light exit 1406 has a protective cover 1407 to protect the end of the light source. The cover 1407 may be plastic, polycarbonate, glass or another appropriate material. Electrodes 1403a and 1403b are provided to power the light source.

In some applications, it may be desired to modify qualities of the light emitted by the light source. For example, the cover 1407 might be filtered plastic that only permits light of a particular wavelength to travel through it. Or the cover 1407 may be a lens or focus dome that focuses or disperses light emitted by the light source. A focus dome may be used to increase light beam intensity or to focus the light beam onto optical fiber, a light guide or another light delivery device.

Figure 14B:
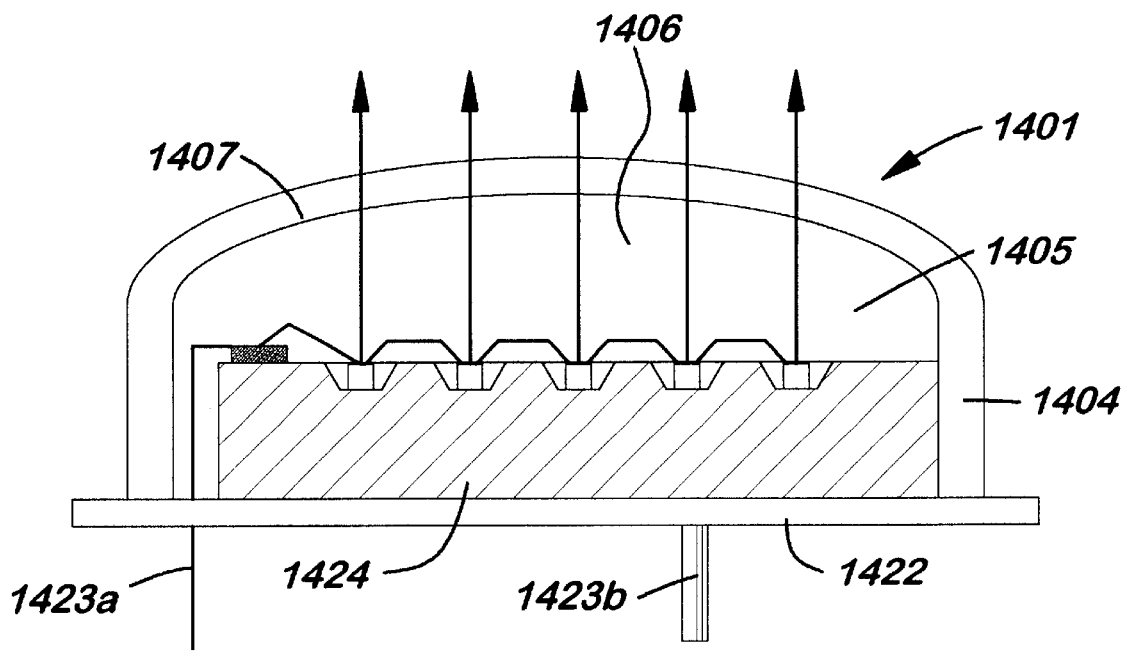

Referring to FIG. 14b, another light source and encasement are discussed. The encasement 1401 is as discussed with reference to FIG. 14a above. The light source 1421 is different from that of FIG. 14a, however. In this case, heat sink in the light source acts as one electrode connection for power supply. The light source 1421 depicted includes a heat sink 1424 seated on top of a heat conductive plate 1422. Electrodes 1423a and 1423b are used to provide electrical power to the light source.

Figure 14C:
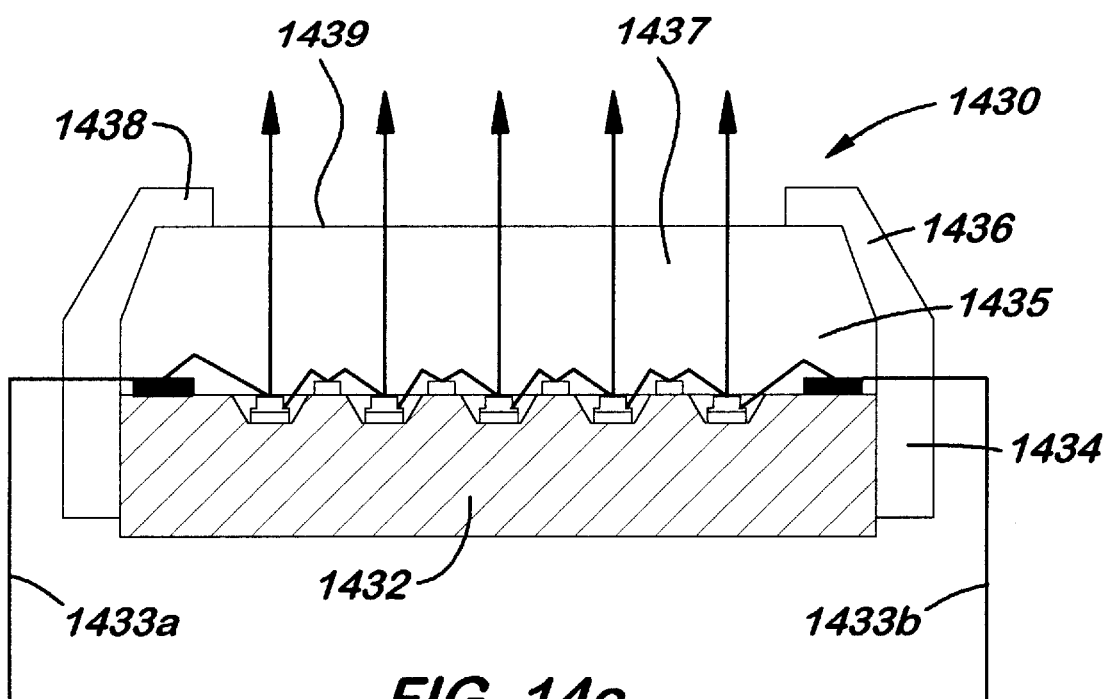
FIG. 14c & 14d depict a portion of a housing of the invention including a transparent window through which light emitted by the light source may exit the housing.

Referring to FIG. 14c, a light source encasement 1430 for a light source 1432 is depicted. The light source 1432 depicted is an LED chip array with an insulating substrate, although any suitable light source could be used. Electrodes 1433a and 1433b are used to provide electrical power to the light source. The light source 1432 is mounted within the bore 1435 of a cylindrical or tubular body 1434 of an encasement 1430. At the distal end of the body, there is a frustoconical section 1436 which terminates in a circular flat section 1438 forming an aperture or light exit 1437. Preferably, a flat circular or disk-shaped cover 1439 is placed across the light exit 1437. The cover 1439 is preferably a window that is transparent to the wavelength of light emitted by the light source. The cover 1439 could be made from clear or filtered plastic, polycarbonate, glass or other appropriate material. The cover 1439 might be filtered plastic that only permits light of a particular wavelength to travel through it. Or the cover 1439 may be a lens or focus dome that focuses or disperses light emitted by the light source. A focus dome may be used to increase light beam intensity or to focus the light beam onto optical fiber, a light guide or another light delivery device. The remainder of the encasement may be made from any material mentioned previously.

Figure 14D:
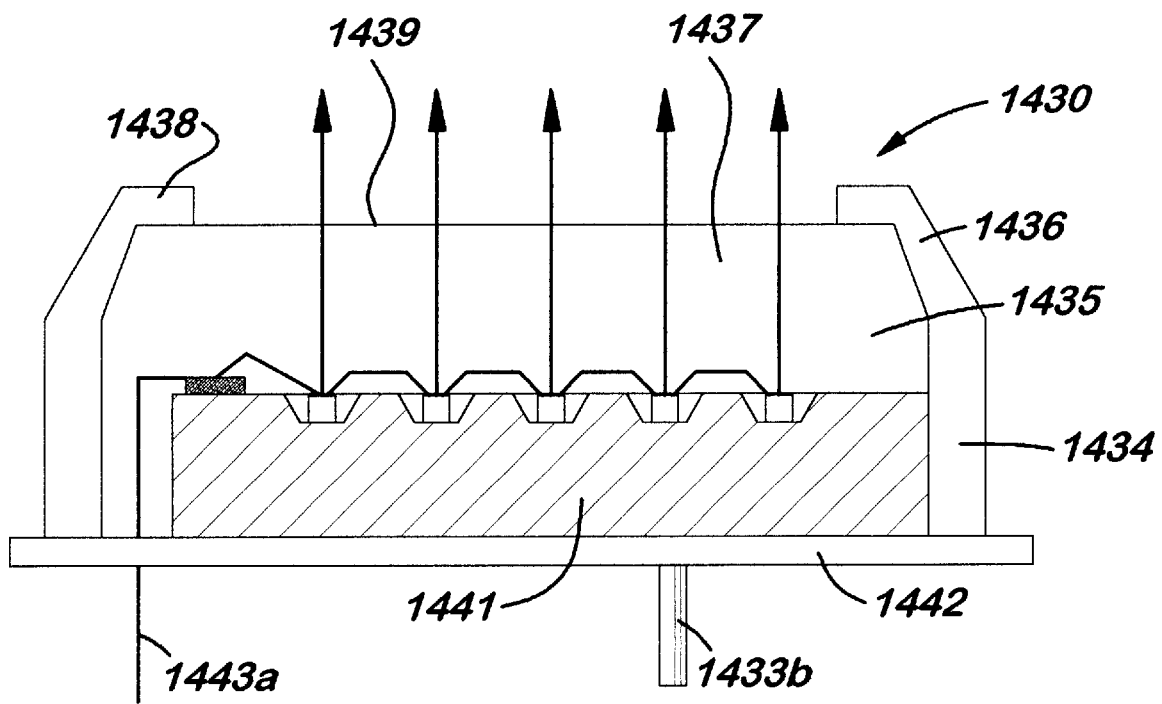

Referring to FIG. 14d, an encasement 1430 as previously discussed for FIG. 14c is provided encasing a light source 1441. The light source 1441 depicted is an LED array with a conductive substrate, although any appropriate light source could be used. The light source 1441 is mounted on a conductive plate 1442. Electrodes 1443a and 1443b are used to power the light source. In this case, heat sink in the light source act as one electrode connection for power supply.

Figure 14E:
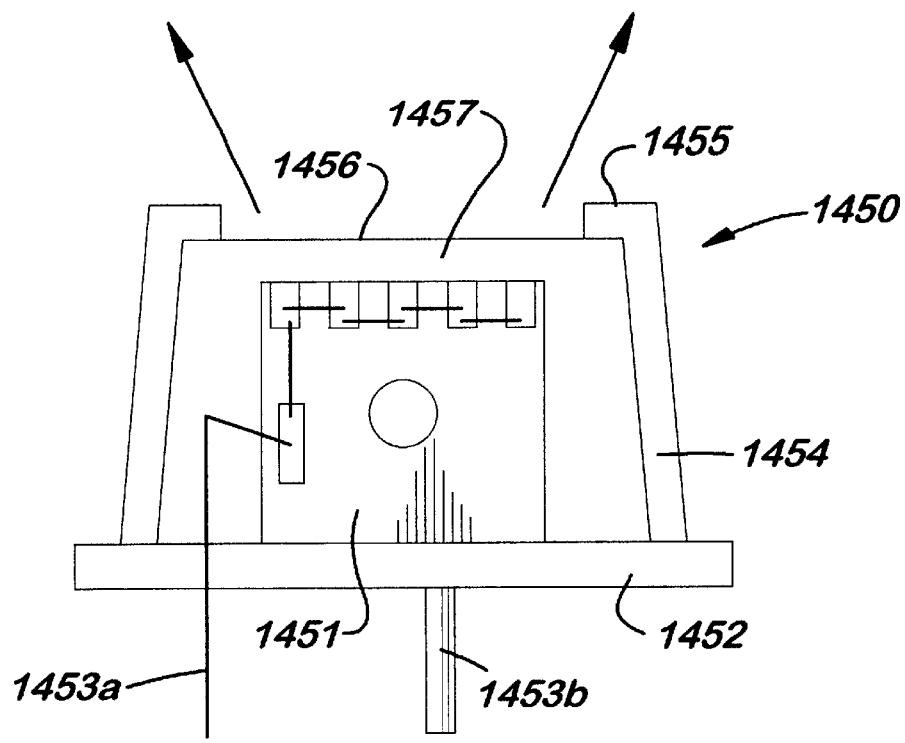
FIG. 14e depicts a portion of a housing of the invention for light emitted by a laser or laser array.

Referring to FIG. 14e, an encasement 1450 for a laser chip or laser chip array 1450 is depicted. The encasement has a conical body 1454, a flat circular portion 1455 at the distal end of the body 1454, and a window 1456 at the distal end of the body 1454. The window 1456 covers the light exit 1457. The window 1456 material is preferably transparent to the light emitted by the light source. The cover 1456 might be filtered plastic that only permits light of a particular wavelength to travel through it. Or the cover 1456 may be a lens or focus dome that focuses or disperses light emitted by the light source. A focus dome may be used to increase light beam intensity or to focus the light beam onto optical fiber, a light guide or another light delivery device. The light source 1451 is depicted as being an array of laser chip on a heat sink. The heat sink of the light source 1451 is seated on top of a heat conductive plate 1452. The body 1454 is sealed with plate 1452. Electrodes 1453a and 1453b extend to the exterior of the encasement for electrical connection.

4. Electronic Control

Figure 15:
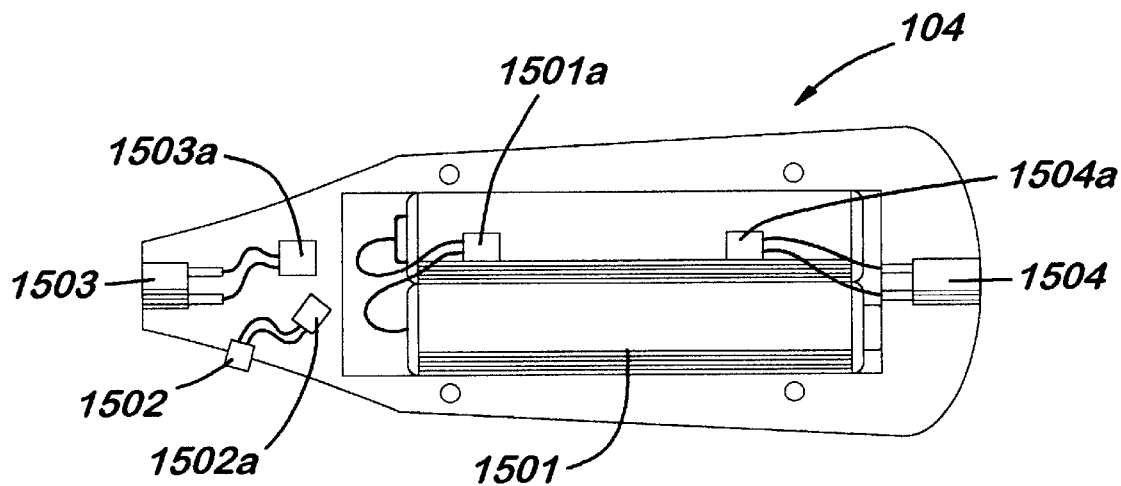
FIG. 15 depicts a cross sectional view of a hand-held portable curing light of the invention.
Figure 16:
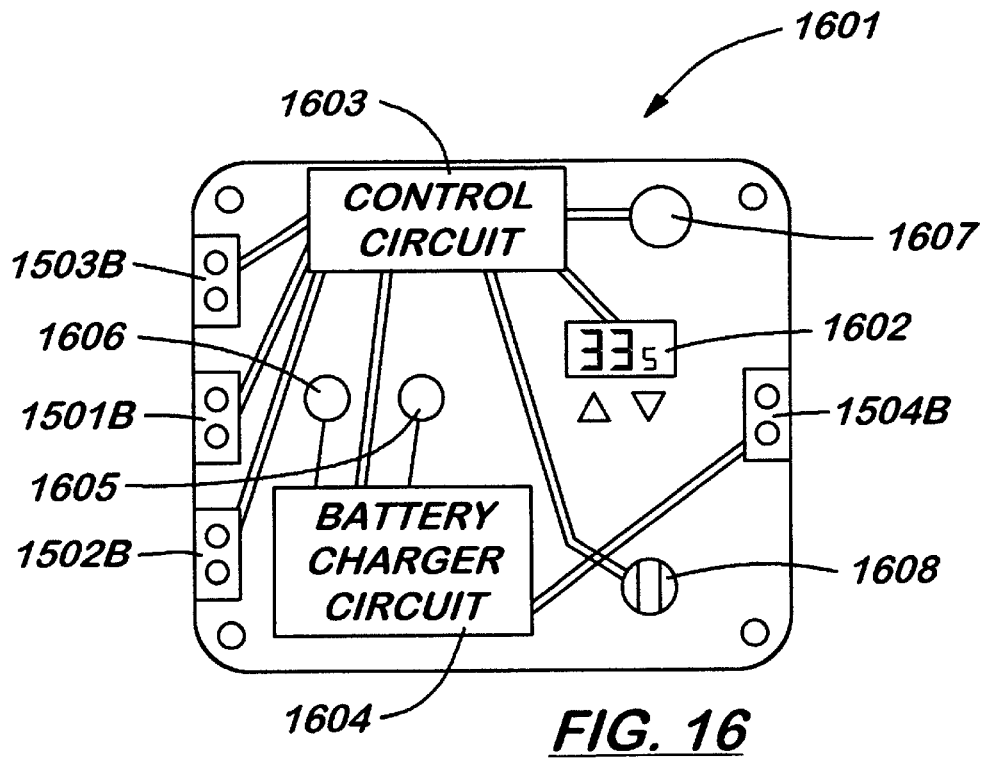
FIG. 16 depicts arrangement of electronic control used in a portable light system of the invention.
Figure 17:
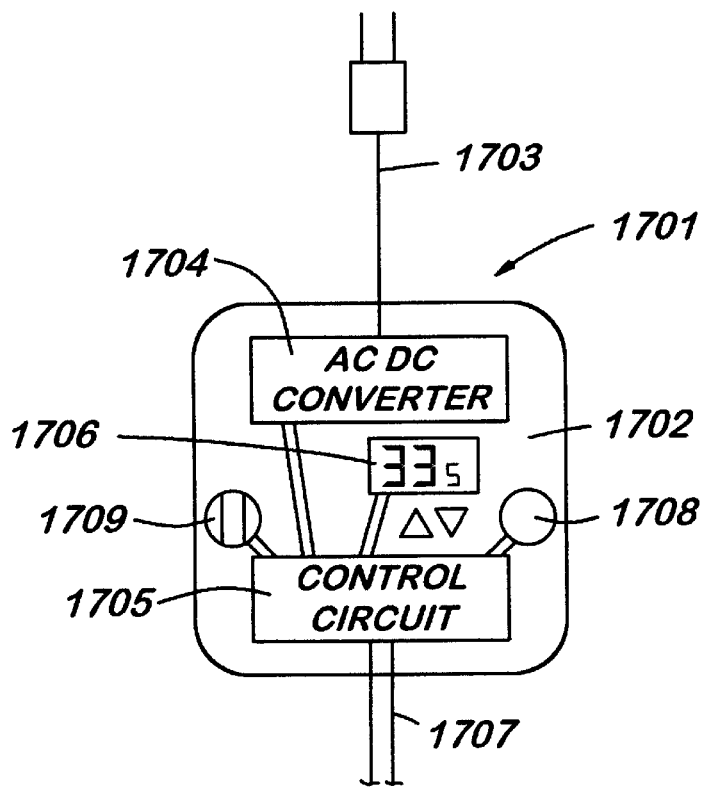
FIG. 17 depicts arrangement of electronic control used in a chair-side light system of the invention

FIG. 15 depicts a cross sectional view of a portion of a hand-held portable curing light of the invention, such as that depicted as section 104 in FIG. 1a. FIG. 16 depicts arrangement of electronic control used in a portable system of the invention, such as a cover that may be installed on the device of FIG. 15. FIG. 17 depicts the arrangement of electronic control that may be used in a chair side curing light system.

In the invention, an electronic control module may be provided to supply and regulate power to the light source. The electronic control module may be located inside of the handle, as depicted in FIG. 1a, or in a separate unit as depicted in FIG. 1b.

Referring to FIG. 15, a hand-held portable curing light system of the invention such as that depicted in FIG. 1a may include a pair of battery pack 1501. An electrical connector 1501*a* is provided for power to be received from the battery pack. A push button switch or trigger switch 1502 may be used to turn battery power to the light source on and off. An electrical connector 1502*a* is provided for the switch 1502. A light module connector 1503 is provided to make electrical contact with a light module. A corresponding electrical connector 1503*a* is also provided. A battery charger receptacle 1504 and corresponding connector 1504*a* are provided so that the batteries of the battery pack 1501 may be recharged.

Referring to FIG. 16, a cover 1601 is depicted for section 104 (previously discussed). The cover 1601 includes a control circuit board 1603 on its underside. In some preferred embodiments, the control circuitry used includes a programmable timer 1602 that may be used to control the duration of light emitted by the light source. The control circuit 1603 handles general system operation. An audible indicator or beeper 1607 is preferably included to audibly indicate to a user when light transmission begins and when light transmission ends. A wavelength selector 1608 is optionally provided to allow the user to choose which wavelength(s) of light are to be emitted from the curing light when a chip array of a plurality of wavelengths is used. A battery charger circuit 1604 may be provided to monitor battery power level and to control battery charging. A first LED 1605 may be provided for battery low indication, and a second LED 1606 may be provided for battery charging indication. Pin connectors 1501*b*, 1502*b*, 1503*b*, and 1504*b* may be provided for connection with connectors 1501*a*, 1502*a*, 1503*a* and 1504*a*, respectively.

In one preferred embodiment of the invention, the operation logic for the various circuitry controlling the system is as follows. Wavelength selector 1608 is set to the desired wavelength if a light source capable of producing multiple wavelength light is used. Power from either the batteries or the battery charger is supplied to control circuit 1603. The control circuit modulates the DC power from battery pack to a desired DC power to light source and timer. The control circuit 1603 is connected to the programmable timer 1602 and switch 1502. After the programmable timer 1602 is set to a desired time, actuating the switch 1502 causes electrical current to be conducted to connector 1503*a* and thus to a light source within a light module, causing the production and emission of curing light. It will also cause beeper 1607 to sound. Curing light will be produced continuously for the period of time for which the timer 1602 was set. Then electrical current will no longer be supplied to the light module and light emission will cease. When light emission ceases, beeper 1607 will sound again.

The battery charger has a sensor circuit to monitor battery voltage and current. When battery power is below a preset value, LED 1605 will be lit to indicate that the battery needs to be charged. When the battery charger is connected to receptacle 1504, the battery charging LED 1606 will be illuminated. Power from the battery charger will charge the batteries 1501*a* and 1501*b*. It will also supply power for operation of the curing light even while the batteries are being charged. When the batteries are fully charged, LED's 1605 and 1606 will be turned off and the battery charger can be disconnected from the curing light. When the battery pack is being charged, the battery charger provides the power to electronic module and light source so that the system is still operative with power from the battery charger.

Referring FIG. 17, a preferred electronic control system for a chair side curing light is depicted. The control module 1701 include a circuit board 1702, a AC power plug 1703, a AC/DC converter 1704, a control circuit 1705, a programmable timer 1706, DC connection 1707 for providing electrical power to a light source, an audible indicator or beeper 1708, and a wavelength selector 1709 if the light source includes chips of different wavelengths. The operation logic of this preferred circuitry is as follows. Wavelength selector 1608 is set to desire selection if light source with chips of different wavelength is used. An AC signal of 110V or 220V and having a frequency of 50–60 Hz is input from plug 1703 to an AC/DC converter 1704. AC/DC converter 1704 converts the AC signal to a desired DC signal, which is then sent to the control circuit 1705. The control circuit 1705 modulates the DC signal from AC/DC converter to a desired DC signal for light module and timer. After the timer 1706 is set to a desired time, a push on a switch in the light module, such as switch 121*b* in FIG. 1*b*, activates the timer and causes the beeper 1708 to produce a sound. Electrical current then is transported to the light module and light is produced and emitted. When the time set on the timer has elapsed, electrical current to the light module is terminated, light production ceases, and the beeper 1708 sounds again.

5. Battery Charger Module

The battery charger can be any AC/DC converter to supply desired current and voltage to charge the battery and to serve as a power source for the curing light system while the battery is being charged. Such battery chargers are common and are available at most electronics stores or customized design factories.

While the present invention has been described and illustrated in conjunction with a number of specific embodiments, those skilled in the art will appreciate that variations and modifications may be made without departing from the principles of the invention as herein illustrated, described, and claimed.

The present invention may be embodied in other specific forms without departing from its spirit or essential characteristics. The described embodiments are to be considered in all respects as only illustrative, and not restrictive. The scope of the invention is, therefore, indicated by the appended claims, rather than by the foregoing description. All changes which come within the meaning and range of equivalency of the claims are to be embraced within their scope.

I claim:

1. A portable curing light system useful for curing light activated composite materials, the portable curing light system comprising:

a light source, said light source including
a primary heat sink, said first heat sink being capable of drawing heat away from a light emitting diode,
at least one well located on said first heat sink, said well being sized and shaped to accommodate a light emitting diode therein,
an annular wall located in said well, said annular wall serving to reflect light in a desired direction,
a light emitting semiconductor chip located on said first heat sink in said well, said chip diode being adjacent to and firmly attached to said primary heat sink so that heat generated by said chip may be drawn away from it by said primary heat sink and conducted to said secondary heat sink from which it may be dissipated, said chip including a substrate selected from the group consisting of insulting substrates and conductive substrates,
a secondary heat sink attached to said first heat sink, said secondary heat sink having a larger volume than said first heat sink and serving to dissipate heat,
a light source housing including a body located about the exterior of said light source, said body serving to contain said light source, a light exit located on said body, said light exit being positioned so that light emitted by said light source can exit said housing and travel to a curing surface without first traveling through a light transport apparatus, a cover covering said light exit, said cover permitting light emitted from said light source to pass through it and travel to a curing surface, a flexible section on said body, said flexible section permitting bending articulation so that said light exit may be oriented toward a curing surface in order to direct light emitted by said light source to a curing surface, said flexible section comprising a soft protective material surrounding at least one bendable wire, and a curing light housing, said curing light housing serving as a handle for a user of the curing light system to use to hold and manipulate the curing light, a battery pack locatable within said housing, said battery pack serving to provide electrical power to said light source, control circuitry located within said curing light housing, said control circuitry serving to control electrical operation of the curing light, and an on and off switch, said on and off switch being located on said curing light housing, said on and off switch serving to selectively provide electrical power to said light source;

wherein light beams from said chip may exit said light source and travel directly to a curing surface without passing through a light transport apparatus.

2. A portable curing light system as recited in claim 1 further comprising:

an array of primary heat sinks located on said secondary heat sink, an array of wells located on said primary heat sinks, and an array of light emitting semiconductor chips, at least some of said chips being located in said wells.

3. A portable curing light system as recited in claim 1 further comprising at least one intermediary island on said heat sink to assist in electrical connection of said chip.

4. A portable curing light system as recited in claim 1 wherein said cover is a focus dome.

5. A portable curing light system as recited in claim 1 wherein said cover is a transparent window.

6. A portable curing light system as recited in claim 1 further comprising a plurality of light emitting semiconductor chips, at least some of said chips being capable of emitting light of a wavelength different from that emitted by others of said chips in order to cause said light source to have the ability to emit more than one wavelength of light.

7. A portable curing light system as recited in claim 6 further comprising a wavelength selector for allowing a user to select the wavelength(s) of light to be emitted.

8. A portable curing light system as recited in claim 1 further comprising a light shield.

9. A portable curing light system useful for curing light activated composite materials, the portable curing light system comprising:

a light source, said light source including a primary heat sink, said first heat sink being capable of drawing heat away from a light emitting diode, a light emitting semiconductor chip located on said first heat sink, said chip being adjacent to and firmly attached to said primary heat sink so that heat generated by said chip may be drawn away from it by said primary heat sink and conducted to a secondary heat sink from which it may be dissipated, a secondary heat sink attached to said first heat sink, said secondary heat sink having a larger volume than said first heat sink and serving to dissipate heat, a light source housing including a body located about the exterior of said light source, said body serving to contain said light source, a light exit located on said body, said light exit being positioned so that light emitted by said light source can exit said housing and travel to a curing surface without first traveling through a light transport apparatus, and a curing light housing, said curing light housing serving as a handle for a user of the curing light system to use to hold and manipulate the curing light, control circuitry located within said curing light housing, said control circuitry serving to control electrical operation of the curing light, and an on and off switch, said on and off switch being located on said curing light housing, said on and off switch serving to selectively provide electrical power to said light source;

wherein light beams from said chips may exit said light source and travel directly to a curing surface without passing through a light transport apparatus.

10. A portable curing light system as recited in claim 9 further comprising:

an array of primary heat sinks located on said secondary heat sink, and an array of light emitting semiconductor chips located on said primary heat sinks.

11. A portable curing light system as recited in claim 1 further comprising at least one intermediary island on said heat sink to assist in electrical connection of said chip.

12. A portable curing light system as recited in claim 1 wherein said cover is a focus dome.

13. A portable curing light system as recited in claim 1 wherein said cover is a transparent window.

14. A portable curing light system as recited in claim 1 further comprising a plurality of light emitting semiconductor chips, at least some of said chips being capable of emitting light of a wavelength different from that emitted by others of said chips in order to cause said light source to have the ability to emit more than one wavelength of light.

15. A portable curing light system as recited in claim 14 further comprising a wavelength selector for allowing a user to select the wavelength(s) of light to be emitted.

16. A portable curing light system as recited in claim 1 further comprising a light shield.

17. A portable curing light system as recited in claim 1 wherein said chip is selected from the group consisting of light emitting diode chips and laser diode chips.

18. A curing light system useful for curing composite materials, the curing light system comprising:

a light source module including a secondary heat sink located in said light source module, a plurality of primary heat sinks located on said secondary heat sink, each of said primary heat sinks having a total volume less than that of said secondary heat sink, a plurality of chips arranged so that each primary heat sink has one chip located on it, said chips being capable of emitting beams of light, and said chips being electrically connected to each other, said chips being selected from the group consisting of surface emitting laser diode chips, edge emitting laser diode chips, and light emitting diode chips, at least one of said chips having a substrate, said substrate being selected from the group consisting of conductive substrates and insulative substrates, and a pair of electrodes in electrical connection with said chips so that said chips may receive electrical power from said electrodes, an electronic control module, said electronic control module serving to provide electrical power to said light source, and a curing light housing, said curing light housing serving as a cover for parts of the curing light;

wherein each of said heat sinks serves to draw heat away from said chips;

wherein light beams from said chips may travel directly to a curing surface without passing through a light transport apparatus.

19. A system as recited in claim 18 wherein said chips are arranged in a linear array wherein the array has a configuration selected from a linear array and an N×M array where N and M are positive integers.

20. A system as recited in claim 18 further comprising a focus dome serving to focus light from said chips into a single substantially coherent light beam to be exposed to a composite material without use of a light guide.

21. A system as recited in claim 18 wherein at least some of said chips are selected from the group consisting of light emitting diode chips and laser chips.

22. A curing light system useful for curing composite materials, the curing light system comprising:

a single solitary light source module including
 a primary heat sink located in said light source module,
 a single solitary light emitting diode chip located on said primary heat sink, said single solitary light emitting diode chip having a substrate, said substrate being selected from the group consisting of electrically insulative substrates and electrically conductive substrates,
 a secondary heat sink located in said light source module, said second heat sink being larger than said primary heat sink, and said primary heat sink being mounted to said secondary heat sink, said heat sinks serving to dissipate heat generated by said chip, and
 a transparent cover protecting said light emitting diode, an electronic control module, said electronic control module serving to provide electrical power to said light source;

wherein dissipation of heat produced by said single light emitting diode chip is achieved by heat transference from said chip to said first heat sink and to said second heat sink without use of a fan; and wherein light beams from said chips may exit said light source and travel directly to a curing surface without passing through a light transport apparatus.

23. A curing light as recited in claim 22 wherein said transparent cover is a focus dome which serves to focus light from said light emitting diode onto a composite material, and wherein said focus dome is designed to be used without use of an accompanying light guide.

24. A curing light system useful for curing composite materials, the curing light system comprising:

a single light source module including
 a first heat sink located in said light source module,
 a single solitary and lone semiconductor chip capable of emitting light located on said first heat sink, said chip having a substrate, said substrate being selected from the group consisting of electrically insulative substrates and electrically conductive substrates,
 a second heat sink located in said light source module, said second heat sink being larger than said first heat sink, and said first heat sink being mounted to said second heat sink so that heat generated by said chip is dissipated to said first heat sink and to said second heat sink so that cooling may be achieved without use of a fan, and
 a transparent cover protecting said chip, and an electronic control module, said electronic control module serving to provide electrical power to said light source;

wherein light from said chip may travel directly to a curing surface without passing through a light transport apparatus.

25. A curing light as recited in claim 24 wherein said first heat sink selected from the group consisting of insulative heat sinks and conductive heat sinks.

26. A curing light as recited in claim 24 wherein said chip is selected from the group of edge emitting diode chips and surface emitting diode chips.

27. A curing light as recited in claim 24 wherein said chip is selected from the group consisting of light emitting diode chips and laser chips.

28. A curing light system useful for curing light activated composite materials, the portable curing light system comprising:

a light source, said light source including
 a heat sink, said heat sink being capable of drawing heat away from a diode laser chip,
 at least one diode laser chip located on said heat sink, said diode laser chip being adjacent to and firmly attached to said heat sink so that heat generated by said diode laser chip may be drawn away by said heat sink, a light source housing including
 a body located about the exterior of said light source, said body serving to contain said light source,
 a light exit located on said body, said light exit being positioned so that light emitted by said light source can exit said housing and travel directly to a curing surface, and
 a cover covering said light exit, said cover permitting light emitted from said light source to pass through it and travel to a curing surface, said light source housing serving as a handle for a user of the curing light system to use to hold and manipulate the curing light, a battery pack locatable within said housing, said battery pack serving to provide electrical power to said light source, control circuitry located within said housing, said control circuitry serving to control electrical operation of the curing light, an on and off switch, said on and off switch being located on said housing, said on and off switch serving to selectively provide electrical power to said light source;

wherein said diode laser chip is an edge emitting diode laser chip that emits light from an edge of the chip; and wherein said edge emitting diode laser chip is located adjacent an edge of one face of said heat sink so that light emitted from said edge emitting diode laser chip is emitted generally perpendicular to said face of said heat sink.

29. A portable curing light system as recited in claim 28 further comprising a flexible section on said housing, said flexible section permitting bending articulation so that said light exit may be oriented toward a curing surface in order to direct light emitted by said light source to a curing surface.

30. A portable curing light system as recited in claim 28 wherein said cover is a focus dome.

31. A portable curing light system as recited in claim 28 wherein said cover is a transparent window which permits light of a wavelength emitted by said laser chip.

32. A portable curing light system as recited in claim 28 further comprising a plurality of laser diode chips, said laser diode chips being selected to cause said light source to have the ability to emit more than one wavelength of light.

33. A portable curing light system as recited in claim 32 further comprising a wavelength selector for allowing a user to select the wavelength(s) of light to be emitted.

34. A portable curing light system as recited in claim 28 further comprising an audio indicator capable of indicating a change in status of light emission of the curing light.

35. A portable curing light system as recited in claim 28 further comprising a light shield.

36. A portable curing light system as recited in claim 28 further comprising an infection control shield for said light source.

* * * * *

UNITED STATES PATENT AND TRADEMARK OFFICE
CERTIFICATE OF CORRECTION

PATENT NO. : 6,331,111 B1
APPLICATION NO. : 09/405373
DATED : December 18, 2001
INVENTOR(S) : Densen Cao Page 1 of 1

It is certified that error appears in the above-identified patent and that said Letters Patent is hereby corrected as shown below:

Column 17
Line 64, replace the phrase "said first heat sink" with "said primary heat sink"
Line 66-67, replace the phrase "said first heat sink" with "said primary heat sink"

Column 18
Line 5, replace the phrase "said first heat sink" with "said primary heat sink"
Line 7, replace the phrase "said first heat sink" with "said primary heat sink"

Column 19
Line 55, replace the phrase "said first heat sink" with "said primary heat sink"
Line 55-56, replace the phrase "said second heat sink" with "said secondary heat sink"
Line 57, replace the phrase "said chips" with "said chip"

Signed and Sealed this

Twenty-second Day of December, 2009

David J. Kappos
*Director of the United States Patent and Trademark Office*